US010745698B2

(12) United States Patent
Rudolph et al.

(10) Patent No.: US 10,745,698 B2
(45) Date of Patent: Aug. 18, 2020

(54) RNA WITH A COMBINATION OF UNMODIFIED AND MODIFIED NUCLEOTIDES FOR PROTEIN EXPRESSION

(71) Applicant: Ethris GmbH, Martinsried (DE)

(72) Inventors: Carsten Rudolph, Munich (DE); Michael Kormann, Erding (DE)

(73) Assignee: ETHRIS GMBH, Planegg (DE)

( * ) Notice: Subject to any disclaimer, the term of this patent is extended or adjusted under 35 U.S.C. 154(b) by 541 days.

(21) Appl. No.: 14/839,886

(22) Filed: Aug. 28, 2015

(65) Prior Publication Data
US 2016/0177295 A1    Jun. 23, 2016

Related U.S. Application Data

(63) Continuation of application No. 14/628,014, filed on Feb. 20, 2015, now abandoned, and a continuation of application No. 14/628,008, filed on Feb. 20, 2015, now abandoned, said application No. 14/628,014 is a continuation of application No. 13/388,140, filed on Apr. 13, 2012, now abandoned, said application No. 14/628,008 is a continuation of application No. 13/388,140, filed as application No. PCT/EP2010/004681 on Jul. 30, 2010, now abandoned.

(30) Foreign Application Priority Data

Jul. 31, 2009    (DE) .................. 10 2009 035 507
Oct. 22, 2009    (DE) .................. 10 2009 050 308

(51) Int. Cl.
| C07H 21/04 | (2006.01) |
| C12N 15/63 | (2006.01) |
| C12N 15/11 | (2006.01) |
| A61K 48/00 | (2006.01) |
| C12N 15/67 | (2006.01) |
| A61L 27/22 | (2006.01) |
| A61K 38/18 | (2006.01) |
| C07K 14/505 | (2006.01) |
| C07K 14/785 | (2006.01) |
| A01K 67/00 | (2006.01) |

(52) U.S. Cl.
CPC .......... *C12N 15/11* (2013.01); *A61K 38/1816* (2013.01); *A61K 48/0066* (2013.01); *A61L 27/227* (2013.01); *C07K 14/505* (2013.01); *C07K 14/785* (2013.01); *C12N 15/67* (2013.01); *A61K 48/00* (2013.01); *C12N 2310/334* (2013.01); *C12N 2310/335* (2013.01); *C12N 2320/30* (2013.01); *C12N 2320/50* (2013.01)

(58) Field of Classification Search
CPC .. C12N 15/11; C12N 15/67; C12N 2310/334; C12N 2310/335; C12N 2320/50; A61K 48/0066
See application file for complete search history.

(56) References Cited

U.S. PATENT DOCUMENTS

| 5,948,681 A | 9/1999 | Scanlin et al. |
| 7,901,711 B1 | 3/2011 | Sung et al. |
| 7,985,426 B1 | 7/2011 | Sung et al. |
| 2003/0083272 A1 | 5/2003 | Wiederholt et al. |
| 2008/0199410 A1 | 8/2008 | Johnson et al. |
| 2010/0041737 A1* | 2/2010 | Naldini ................ C12N 15/635 514/44 R |
| 2010/0047261 A1 | 2/2010 | Hoerr et al. |
| 2011/0142890 A1 | 6/2011 | Fernandez |
| 2012/0009222 A1 | 1/2012 | Nguyen et al. |
| 2015/0290288 A1 | 10/2015 | Rudolph et al. |
| 2015/0291678 A1 | 10/2015 | Rudolph et al. |

FOREIGN PATENT DOCUMENTS

| CA | 2552241 A1 | 7/2005 |
| WO | WO1995/027721 | 10/1995 |
| WO | WO-199914346 A2 | 3/1999 |
| WO | WO-200724708 A2 | 3/2007 |
| WO | WO2008/052770 A2 | 5/2008 |
| WO | WO-2009127230 A1 | 10/2009 |

OTHER PUBLICATIONS

Alexopoulou et al., "Recognition of Double-Stranded RNA and Activation of NF-kB by Toll-Like Receptor 3," Nature 413:732-738 (2001).
Alleyne et al., "Preferential Axial Flow during High-Frequency Oscillations: Effects of Gas Density," The American Physiological Society 542-547 (1989).
Aneja et al., "Phage phiC31 Integrase-Mediated Genomic Integration and Long-Term Gene Expression in the Lung after Nonviral Gene Delivery," J Gene Med., 9:967-975 (2007).
Bivas-Benita et al., "Non-Invasive Pulmonary Aerosol Delivery in Mice by the Endotracheal Route," European Journal of Pharmaceutics and Biopharmaceutics 61:214-218 (2005).
Brown et al., "Endogenous MicroRNA can be Broadly Exploited to Regulate Transgene Expression According to Tissue, Lineage and Differentiation Sate," Nature Biotechnology 25(12):1457-1467 (2006).
Brown et al., "Endogenous MicroRNA Regulation Suppresses Transgene Expression in Hematopoietic Lineages and Enables Stable Gene Transfer," Nature Medicine 12(5):585-591 (2006).

(Continued)

*Primary Examiner* — Quang Nguyen
(74) *Attorney, Agent, or Firm* — Morse, Barnes-Brown & Pendleton, P.C.; Lisa M. Warren, Esq.

(57) ABSTRACT

The invention relates to a polyribonucleotide with a sequence that codes a protein or protein fragment, wherein the polyribonucleotide comprises a combination of unmodified and modified nucleotides, wherein 5 to 50% of the uridine nucleotides and 5 to 50% of the cytidin nucleotides are modified uridine nucleotides or modified cytidin nucleotides.

7 Claims, 23 Drawing Sheets
Specification includes a Sequence Listing.

(56) References Cited

OTHER PUBLICATIONS

Clark et al., "Targeted Disruption of the Surfactant Protein B Gene Disrupts Surfactant Homeostasis, Causing Respiratory Failure in Newborn Mice," Proc. Natl. Acad. Sci. USA 92:7794-7798 (1995).
Dames et al., "Targeted Delivery of Magnetic Aerosol Droplets to the Lung," Nature Nontechnology www.nature.com/naturenanotechnology (2007).
Diebold et al., "Innate Antiviral Responses by Means of TLR7-Mediated Recognition of Single-Stranded RNA," Science 303:1529-1531 (2004).
Glasser et al., "cDNA and Deduced Amino Acid Sequence of Human Pulmonary Surfactant-Associated Proteolipid SPL(Phe)," Proc. Natl. Acad. Sci. USA 84:4007-4011 (1987).
Griese et al., "Expression Profiles of Hydrophobic Surfactant Proteins in Children with Diffuse Chronic Lung Disease," Respiratory Research 6:80-90 (2005).
Hamvas et al., "Lung Transplantation for Treatment of infants with Surfactant Protein B Deficiency," The Journal of Pediatrics 130(2):231-239 (1997).
Hantos et al., "Mechanical Impedances of Lungs and Chest Wall in the Cat," The American Physiological Society 427-433 (1992).
Heil et al., "Species-Specific Recognition of Single-Stranded RNA via Toll-like Receptor 7 and 8," Science 303: 1526-1529 (2004).
Holtkamp et al., "Modification of Antigen-Encoding RNA Increases Stability, Translational Efficacy, and T-Cell Stimulatory Capacity of Dendritic Cells," Blood 108(13):4009-4017 (2006).
Ikegami et al., "Reversibility of Lung Inflammation Caused by SP-B Deficiency," Am J Physiol Lung Cell Mol. Physiol., 289:L962-L970 (2005).
Kariko et al., "Incorporation of Pseudouridine Into mRNA Yields Superior Nonimmunogenic Vector With Increased Tranlational Capacity and Bilological Stability," Molecular Therapy 16(11):1833-1840 (2008).
Kariko et al., "Suppression of RNA Recognition by Toll-like Receptors: The Impact of Nucleoside Modification and the Evolutionary Origin of RNA," Immunity 23:165-175 (2005).
McKenna et al., "Purification and Characterization of Transcribed RNAs using Gel Filtration Chromatography," Nature Protocols 2(12):3270-3277 (2007).
Melton et al., "SP-B Deficiency Causes Respiratory Failure in Adult Mice," Am. J Physiology Lung Cell Mol. Physiol. 285:L543-L549 (2003).
Nogee et al., "Brief Report: Deficiency of Pulmonary Surfactant Protein B in Congenital Alveolar Proteinosis," The New England Journal of Medicine 328(6):406-410 (1993).
Pfaffl et al., "Relative Expression Software Tool (REST ©) for Group-Wise Comparison and Statistical Analysis of Relative Expression Results in Real-Time PCR," Nucleic Acids Research 30(9):36-45 (2002).
Pillow et al., "Overexpression of TGF-α Increases Lung Tissue Hysteresivity in Transgenic Mice," J. Appl. Physiol., 91:2730-2734 (2001).
Read et al., "A Versatile Reducible Polycation-Based System for Efficient Delivery of a Broad Range of Nucleic Acids," Nucleic Acids Research 33(9):1-16 (2005).
Schuessler et al., "A Computer-Controlled Research Ventilator for Small Animals: Design and Evaluation," IEEE Transactions on Biomedical Engineering 42(9):860-866 (1995).
Sly et al., "Volume Dependence of Airway and Tissue Impedances in Mice," J. Appl. Physiology 94:1460-1466 (2003).
Weaver et al., "Processing of Hydrophobic Pulmonary Surfactant Protein B in Rat Type II Cells," The American Physiological Society L100-L108 (1989).
Weiss et al., "Transient Increase Junction Permeability: An Additional Mechanism for Enhancement of Lung Transgene Expression by Perfluorochemical Liquids," Molecular Therapy 8(6):927-935 (2003).
Whitsett et al., "Hydophobic Surfactant Proteins in Lung Function and Disease," New England Journal of Medicine 347(26):2141-2148 (2002).
Yoneyama et al., "The RNA Helicase RIG-I Has an Essential Function in Double-Stranded RNA-Induced Innate Antiviral Responses," Nature Immunology 5(7): 730-737 (2004).
Guo, Zongru, "IV. Carbocyclic Nucleoside," *Medical Chemistry, China Medical Science and Technology Press*, ISBN: 7-5067-1163-X, p. 256-358.
Kormann, et al., "Expression of Therapeutic Proteins After Delivery of Chemically Modified mRNA in Mice," *Nature Biotechnology* 29.2 (2011): 154-157.
Rosas-Taraco, Adrian G., et al. "Intrapulmonary delivery of XCL1-targeting small interfering RNA in mice chronically infected with *Mycobacterium tuberculosis*." American journal of respiratory cell and molecular biology 41.2 (2009): 136-145.
Office Action issued in European Patent Application No. 10742089.5 dated Jun. 5, 2014.

* cited by examiner

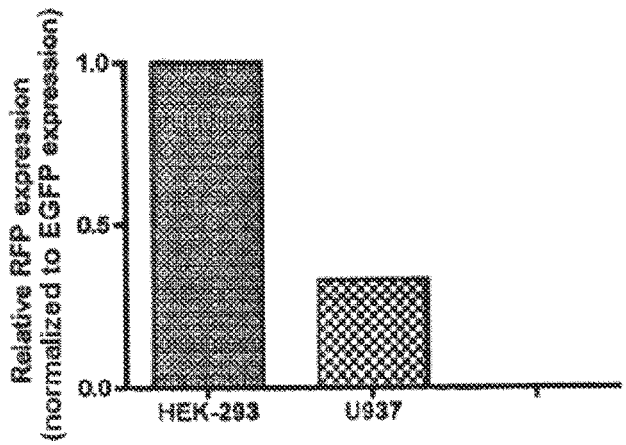

Figure 17B

```
GGATCCATGGCCTCCTCCGAGGACGTCATCAAGGAGTTCATGCGCTTCAAGGTG
CGCATGGAGGGCTCCGTGAACGGCCACGAGTTCGAGATCGAGGGCGAGGGCGA
GGGCCGCCCCTACGAGGGCACCCAGACCGCCAAGCTGAAGGTGACCAAGGGCG
GCCCCCTGCCCTTCGCCTGGGACATCCTGTCCCCCCAGTTCCAGTACGGCTCCAA
GGTGTACGTGAAGCACCCCGCCGACATCCCCGACTACAAGAAGCTGTCCTTCCC
CGAGGGCTTCAAGTGGGAGCGCGTGATGAACTTCGAGGACGGCGGCGTGGTGAC
CGTGACCCAGGACTCCTCCCTGCAGGACGGCTGCTTCATCTACAAGGTGAAGTTC
ATCGGCGTGAACTTCCCCTCCGACGGCCCCGTAATGCAGAAGAAGACTATGGGC
TGGGAGGCCCTCCACCGAGCGCCTGTACCCCCGCGACGGCGTGCTGAAGGGCGAG
ATCCACAAGGCCCTGAAGCTGAAGGACGGCGGCCACTACCTGGTGGAGTTCAAG
TCCATCTACATGGCCAAGAAGCCCGTGCAGCTGCCCGGCTACTACTACGTGGACT
CCAAGCTGGACATCACCTCCCACAACGAGGACTACACCATCGTGGAGCAGTACG
AGCGCGCCGAGGGCCGCCACCACCTGTTCCTGTAGCTAGAGTCGACTCCATAAA
GTAGGAAACACTACACGATTCCATAAAGTAGGAAACACTACAACCGGTTCCATA
AAGTAGGAAACACTACATCACTCCATAAAGTAGGAAACACTACACAAAAAAAA
AAAAAAAAAAAAAAAAAAAAAAAAAAAAAAAAAAAAAAAAAAAAAAAAAAAA
AGATATC
```

Figure 18

RNA WITH A COMBINATION OF UNMODIFIED AND MODIFIED NUCLEOTIDES FOR PROTEIN EXPRESSION

CROSS REFERENCE TO RELATED APPLICATIONS

This application is a continuation of U.S. Ser. No. 14/628,014, filed Feb. 20, 2015, and U.S. Ser. No. 14/628,008, filed Feb. 20, 2015, each of which is a continuation application of U.S. Ser. No. 13/388,140, filed Apr. 13, 2012, which is a national stage filing under 35 U.S.C. § 371 of International Application No. PCT/EP2010/004681, filed Jul. 30, 2010, which claims priority to German Patent Application No. 10 2009 035 507.3, filed Jul. 31, 2009, and German Patent Application No. 10 2009 050 308.0, filed Oct. 22, 2009. The foregoing applications are hereby incorporated by reference in their entirety.

SEQUENCE LISTING

The instant application contains a Sequence Listing that has been submitted in ASCII format via EFS-Web and is hereby incorporated by reference in its entirety. Said ASCII file, created on Mar. 9, 2016, is named 110016-0009-305-SL-Sequence-Listing.txt and is 2,185 bytes in size.

The invention relates to a polyribonucleotide, in particular messenger RNA, which contains a combination of unmodified and modified nucleotides, for protein expression and the use of such RNAs for the therapy of diseases and for diagnostic procedures.

Messenger RNAs (mRNA) are polymers which are built up of nucleoside phosphate building blocks mainly with adenosine, cytidine, uridine and guanosine as nucleosides, which as intermediate carriers bring the genetic information from the DNA in the cell nucleus into the cytoplasm, where it is translated into proteins. They are thus suitable as alternatives for gene expression.

The elucidation of the biochemical processes in the cell and the elucidation of the human genome have revealed connections between deficient genes and diseases. Hence there has long been the desire to heal diseases due to deficient genes by gene therapy. The expectations were high, but attempts at this as a rule failed. A first approach to gene therapy consisted in bringing the intact DNA of a deficient or defective gene into the cell nucleus in a vector in order to achieve the expression of the intact gene and thus the provision of the missing or defective protein. These attempts were as a rule not successful and the less successful attempts were burdened with substantial side effects, in particular elevated tumorigenesis.

Furthermore, there are diseases which are due to a lack of proteins or a protein defect, without this being attributable to a genetic defect. In such a case also, consideration is being given to producing the relevant proteins in vivo by administration of DNA. The provision of factors which play a part in the metabolism and are destroyed or inhibited for pathological or non-pathological reasons could also be effected by a zero or low side effect nucleic acid therapy.

The use has also already been proposed of mRNAs for the therapy of hereditary diseases in order to treat gene defects which lead to diseases. The advantage in this is that the mRNA only has to be introduced into the cytoplasm of a cell, but does not have to be inserted into the nucleus. Insertion into the nucleus is difficult and inefficient; moreover there is a considerable risk of the chromosomal DNA being altered if the vector or parts thereof become incorporated into the genome.

Admittedly it could be shown that in vitro transcribed messenger RNA can in fact be expressed in mammalian tissue, however further hurdles arose in the attempt to use mRNA for the therapy of diseases. The lack of stability of the mRNA had the effect that the desired protein could not be made available in sufficient quantity in the mammalian tissue. A further substantial disadvantage resulted from the fact that mRNA triggers considerable immunological reactions. It is presumed that these strong immune reactions arise through binding to Toll-like receptors such as TLR3, TLR7, TLR8 and helicase RIG-1.

In order to prevent an immunological reaction, it was proposed in WO 2007/024708 to use RNA wherein one of the four ribonucleotides is replaced by a modified nucleotide. In particular, it was investigated how mRNA behaves when the uridine is totally replaced by pseudouridine. It was found that such an RNA molecule is significantly less immunogenic. However, the biological activity of these products was not yet sufficient for successful therapy. Moreover, it was found that RNA sequences wherein two or more types of nucleotides are fully replaced by modifications can only be made with difficulty or not at all.

In order to be able to provide the body with necessary or beneficial proteins and/or to treat a disease due to missing or deficient proteins with nucleic acids, it is desirable to have a nucleic acid available which can transfect cells, which remains stable in the cell for long enough and provides a sufficient quantity of protein, so that excessively frequent administration is avoided. At the same time, however, this nucleic acid must not cause immunological reactions to a significant extent.

Hence a purpose of the present invention was to provide an agent which is suitable for the therapy of diseases caused by deficient or defective genes or diseases caused by missing or defective proteins, or which can in vivo produce necessary or beneficial proteins, which triggers a markedly diminished or no immune response, is stable in a physiological environment, i.e. is not degraded immediately after administration and overall is suitable as an agent for therapy. Further, it was a purpose of the invention to provide an agent for the therapy of diseases which can be positively influenced by in vivo production of proteins.

This problem is solved with a polyribonucleotide as defined in claim 1. Particularly suitable is mRNA which encodes a protein or protein fragment, a defect or lack whereof is disadvantageous to the body, or expression whereof is of advantage to the body. When the term "polyribonucleotide" or "mRNA" is used below, unless the context states otherwise, it should always be assumed that this is a polyribonucleotide or an mRNA which encodes a protein or protein fragment which is connected with an illness or lack, as described above, or encodes a protein or protein fragment which is beneficial or supportive to the body.

It has surprisingly been found that the aforesaid problems can be solved with ribonucleic acid or polyribonucleotides (also generally referred to below as RNA), in particular with messenger RNA (mRNA), if an RNA is used which contains both unmodified and also modified nucleotides, it being essential that a predetermined content of the uridine and the cytidine nucleotides respectively is present in modified form.

Further, it has surprisingly been observed that RNA wherein two types of nucleotides are each partially replaced with modified nucleotides shows high translation and transfection efficiency, i.e. the RNA transfects more cells and produces more of the encoded protein per cell than was possible with known RNA. In addition, the RNA modified according to the invention is active for longer than the RNA or unmodified RNA known from the state of the art.

The advantages achieved with the RNA according to the invention are obtained neither with unmodified nor with fully modified RNA. It has been found that both diminished immunogenicity and also increased stability can be achieved if the content of modified uridine and cytidine nucleotides in the mRNA is specifically set and is at least 5% and not more than 50% for each. If an mRNA with no modifications is used, this is extremely immunogenic, while when all uridine and cytidine nucleotides are present in modified form the biological activity is too low for use for therapeutic purposes to be possible. RNA in which the content of modified nucleotides is very high can be produced under very difficult conditions or not at all. Thus it has been established that a nucleotide mixture which contains only pseudouridine instead of uridine and only modified cytosine and/or modified adenosine cannot yield any RNA sequence. Surprisingly, however, RNA sequences which are modified in the manner according to the invention can be produced easily with reasonable efficiency.

In addition, it has been found that the nature of the modification is critical. The mRNAs modified according to the invention show low immunogenicity and have a long lifetime.

It has been found that the stability of the RNA according to the invention is markedly increased compared to previously used nucleic acids. Thus it has been established that the mRNA according to the invention is detectable 10 days after the transfection in a quantity 10 times higher than unmodified RNA. As well as high transfection rates, the increased lifetime above all enables the use of the mRNA according to the invention for therapeutic purposes, since the high stability and hence long lifetime makes it possible to effect administration at longer time intervals which are thus also acceptable to the patients.

Thus according to the invention a particularly advantageous agent for therapeutic purposes is provided. The RNA according to the invention fulfills the requirements that are placed on a product to be used in therapy: as RNA it needs only to be introduced into the cytoplasm and not into the cell nucleus to develop its activity, the danger of integration into the genome does not exist, the type of modification according to the invention largely prevents an immune reaction and in addition the modification protects the RNA from rapid degradation. Hence with the RNA according to the invention it is possible to generate or to regenerate physiological functions in tissues, e.g. to restore in vivo functions which had failed owing to a deficient or defective gene, and hence to treat diseases caused by deficient or defective genes. Further, it has surprisingly been found that polyribonucleotides according to the invention can favorably influence diseases in that proteins are produced in vivo which can directly or indirectly have an influence on the course of the disease. Hence according to the invention polyribonucleotides can also be provided which encode factors which are beneficial and supportive to the body in general or in a specific situation, e.g. growth factors, angiogenesis factors, stimulators, inducers, enzymes or other biologically active molecules.

The invention is explained in more detail in the following description and the attached diagrams.

FIGS. 1A-1C show the effect of different nucleotide modifications on the immunogenicity and stability of various mRNAs. FIG. 1A is a diagram on which the TNF-α level after administration of various RNAs with differently modified nucleotides is plotted. Unmodified and up to 25% singly modified RNA leads to a high level of inflammatory markers and shows the high immunogenicity of this RNA, while for RNA doubly modified according to the invention the inflammatory markers are present in tolerable amount. FIGS. 1B and 1C show the biological activity (transfection efficiency and expression) of mRNA modified in various ways in human cells and mouse cells as the percentage of the cells positive for red fluorescing protein (RFP) and the quantity of RFP per cell. The diagrams show that the proteins encoded by unmodified, singly modified and completely modified RNA can only be detected at a lower percentage content, while the RNA partly doubly modified according to the invention yields significantly higher quantities of protein owing to its greater stability.

FIGS. 2A-D show the higher stability and longer duration of expression for multiply modified mRNA. FIGS. 2A and 2B each show diagrams on which the duration of expression of various modified and unmodified mRNAs is plotted. FIG. 2C shows data for RNA immunoprecipitation for unmodified RNA, singly modified RNA and multiply modified RNA. FIG. 2D shows diagrams in which the immunogenicity of various mRNAs after in vivo intravenous administration is plotted. The data show that an RNA doubly modified according to the invention displays a combination of high stability and low immunogenicity.

FIGS. 3A-3I show various test results which were obtained after intratracheal aerosol application of modified SP-B mRNA in SP-B conditionally deficient mice. FIG. 3A shows bioluminescence images of the lung of mice treated with unmodified RNA and multiply modified RNA. It can clearly be seen that a sufficient quantity of protein is still also expressed after 5 days only by RNA modified according to the invention, while with unmodified RNA the expression is already low after 3 hours. FIG. 3B shows a diagram in which the flux is plotted against the time after transfection. It can clearly be discerned that the modification according to the invention prolongs the duration of expression. FIG. 3C shows the dosing scheme for SP-B mRNA. FIG. 3D shows a diagram which presents the survival rate for mice which were treated with modified mRNA compared to mice which were treated with control mRNA, the survival rate in mice treated with RNA according to the invention being markedly longer. FIG. 3E shows an immunostaining in which it can be seen that with RNA according to the invention which encodes SP-B the SP-B in SP-B deficient mice could be reconstituted. FIG. 3F shows as the result of a semi-quantitative Western blot analysis the distribution of proteins in cell-free BALF supernatant. FIGS. 3G and H show images of lung histology preparations and bronchoalveolar lavage preparations from mice treated according to 3C. While lung and lavage preparations from mice which had received control RNA showed the lung damage usual for SP-B deficiency, the preparations from mice treated with RNA according to the invention were non-pathological. FIG. 3I shows a diagram concerning the lung tolerance over time. The lung function was retained over a longer period on treatment with RNA according to the invention, while lung damage was found in animals treated with control RNA.

Figure 6:
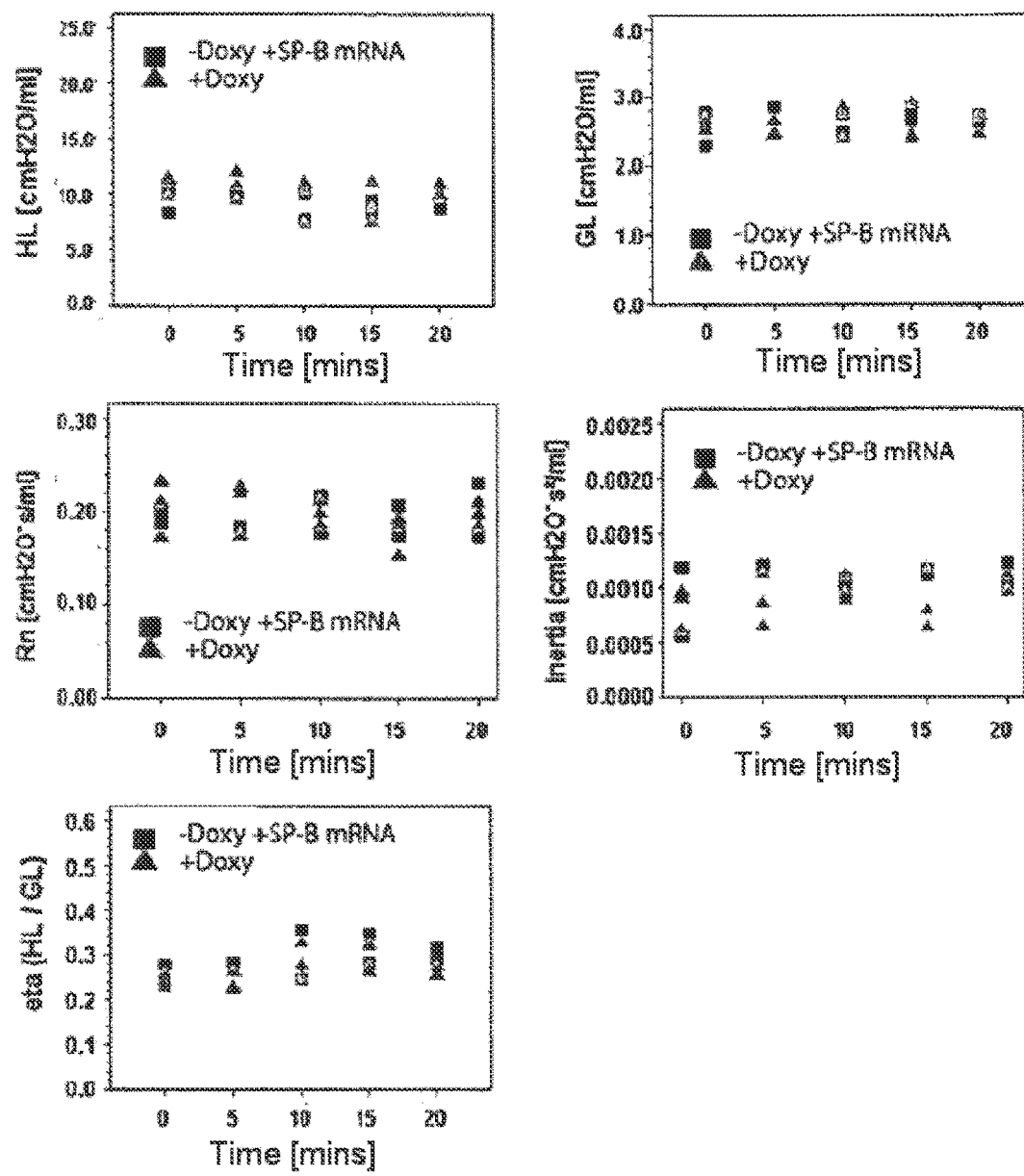

FIG. 6 shows diagrams in which different typical lung parameters are plotted for mice treated with different mRNAs according to the invention. The parameters are tissue elasticity (HL), tissue damping (GL), tissue inertia, airway resistance (Rn) and lung tissue composition Eta (GL/HL). For the RNAs according to the invention, none of the parameters was worsened compared to the positive control group.

Figure 7:
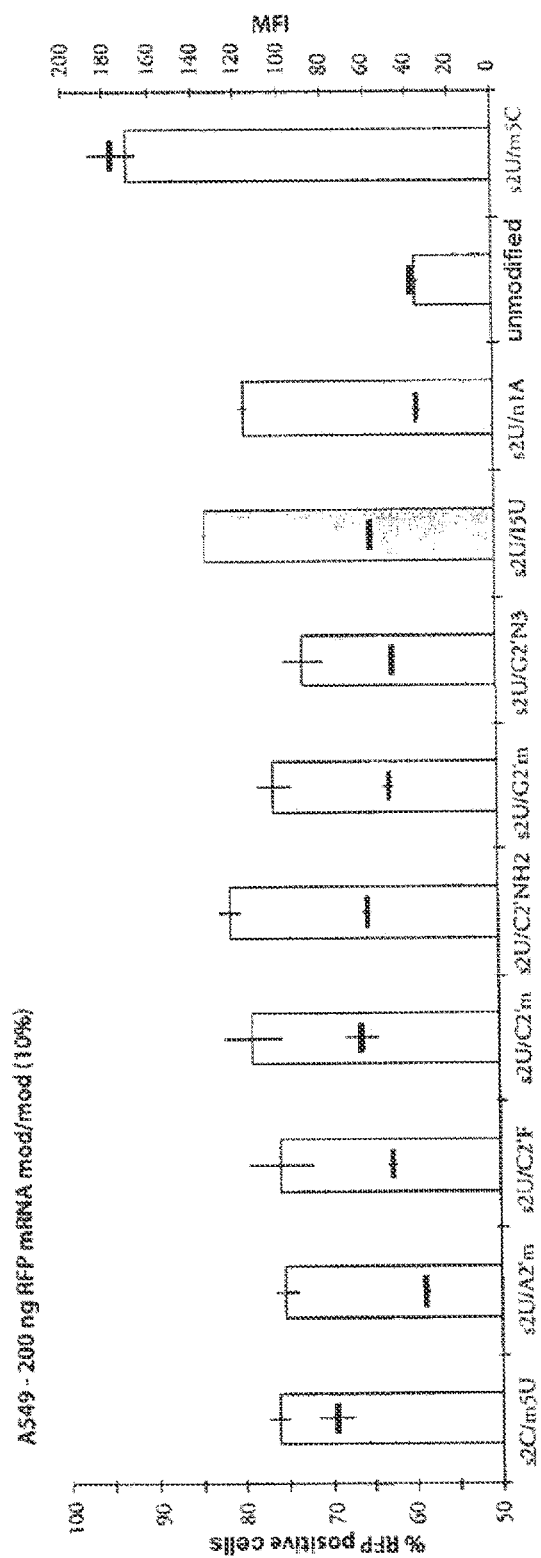

FIG. 7 shows the expression capacity of differently modified mRNA in a diagram in which the percentage content of RFP positive cells is plotted for mRNA with a different content of modified nucleotides. The comparison shows that only mRNA modified according to the invention leads to long-lasting expression, while mRNA modified not according to the invention expresses to a lesser extent both in human cells and also in mouse cells.

Figure 8:
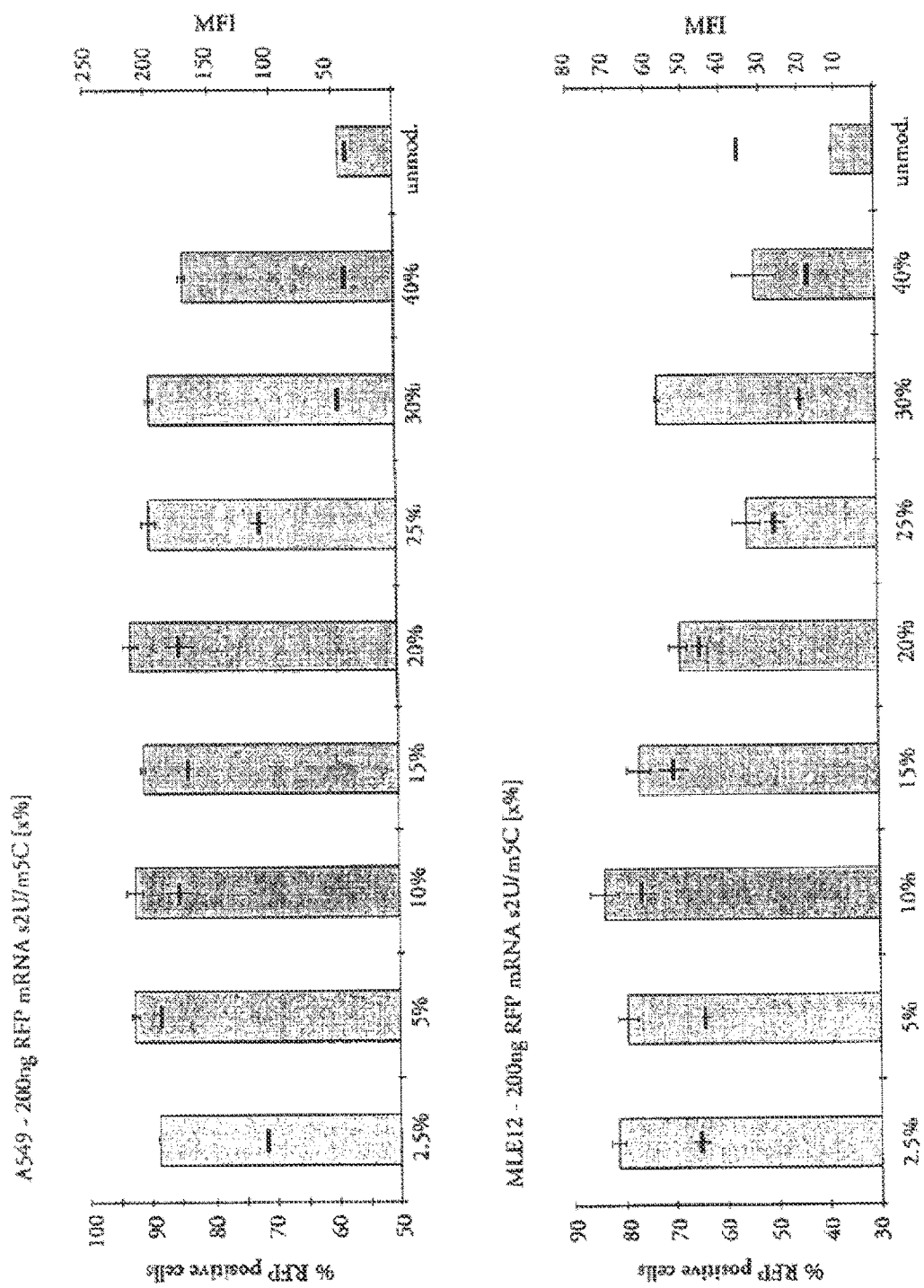

FIG. 8 shows the expression capacity of differently modified mRNA in a diagram in which the percentage content of RFP positive cells is plotted for mRNA with differently modified nucleotides. The comparison shows that only mRNA modified according to the invention leads to long-lasting expression, while mRNA modified not according to the invention expresses to a lesser extent both in human cells and also in mouse cells.

Figure 9:
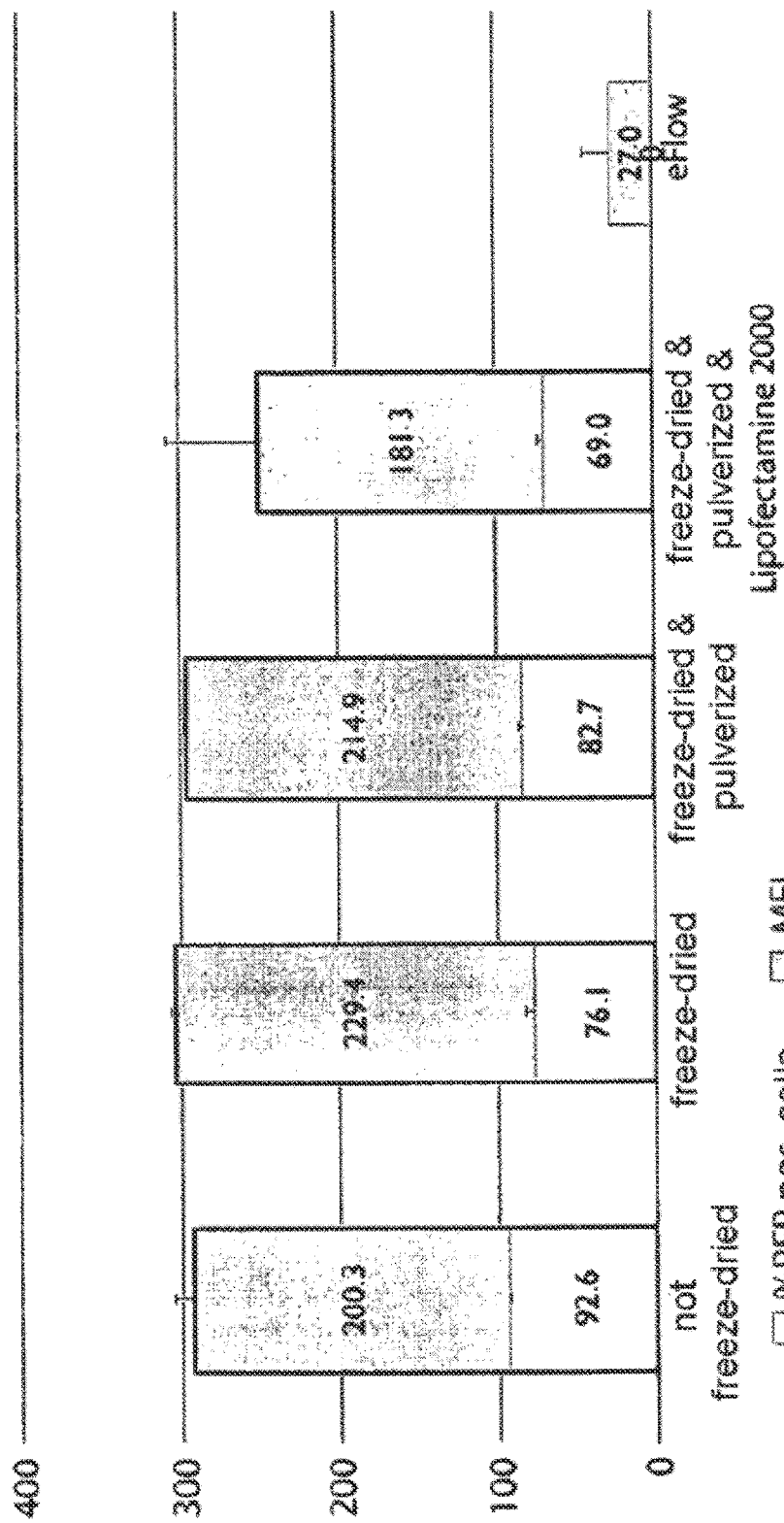

FIG. 9 shows the stability of freeze-dried RNA according to the invention.

Figure 10A:
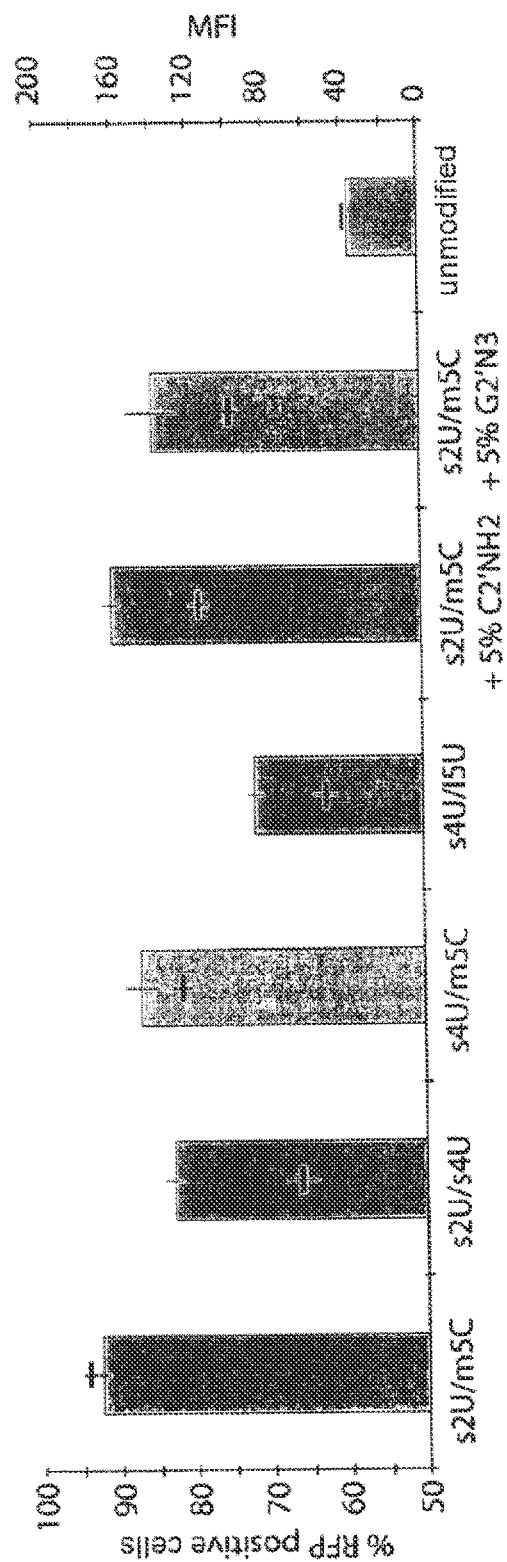
Figure 10B:
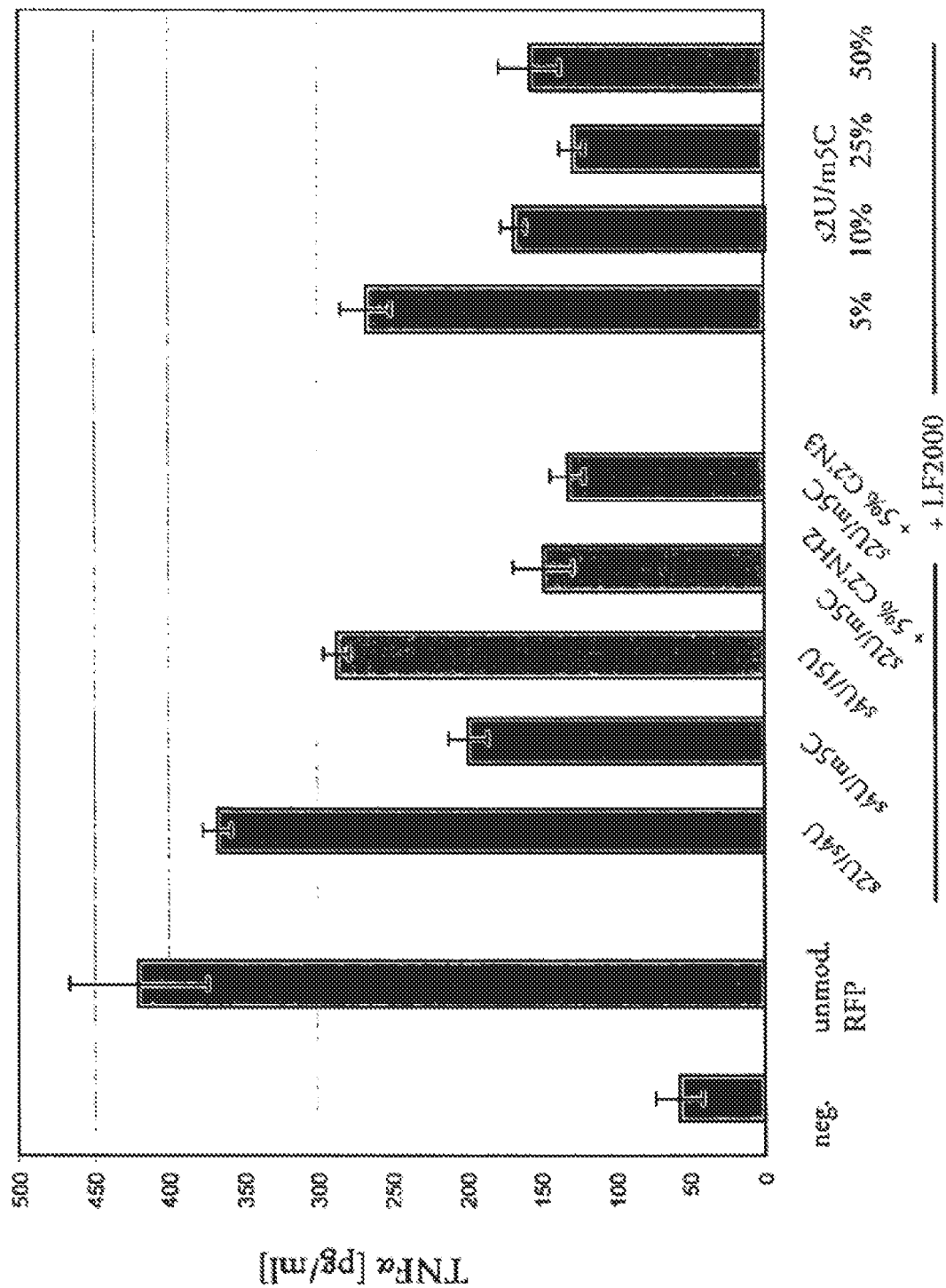

FIG. 10A shows a diagram in which the transfection efficiency is plotted for various modified nucleotides. It can clearly be discerned that the highest transfection efficiency is attained with RNA wherein 10% of the uridine nucleotides and 10% of the cytidine nucleotides and optionally also 5% of further nucleotides are modified. FIG. 10B shows a diagram in which the TNF-α production as a marker for the immunological reaction is plotted for RNA with differently modified nucleotides. These are the results of an ELISA of human PBMCs which were each transfected with 5 μg of mRNA. Unless otherwise stated, the modification rate was 10% in each.

It is clearly discernible that RNA wherein between 5 and 50% of the uridine nucleotides and cytidine nucleotides are modified has a markedly reduced immunogenicity compared to unmodified RNA.

Figure 11A:
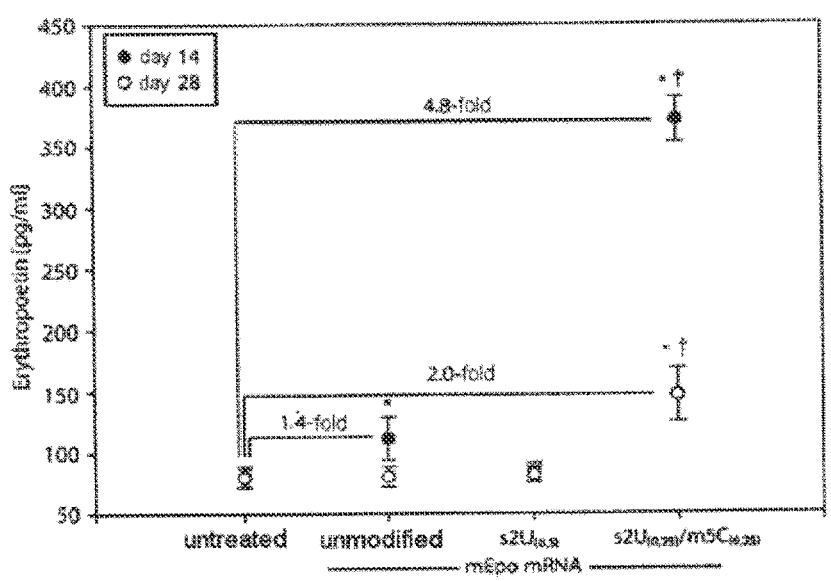

FIGS. 11A-11D show the results of various tests with which the stability and immunogenicity of mRNA modified according to the invention, which encodes EPO, was measured. FIG. 11A shows the content of erythropoietin which is detectable 14 days after administration of mRNA encoding EPO which is modified in different ways. It is clearly discernible that after 14 days the content of EPO in mice into which mRNA modified according to the invention was injected is 4.8 times higher than in untreated mice, but also 4.8 times higher than in mice treated with unmodified RNA and is still 2.5 times higher than in mice treated with singly modified RNA.

Figure 11B:
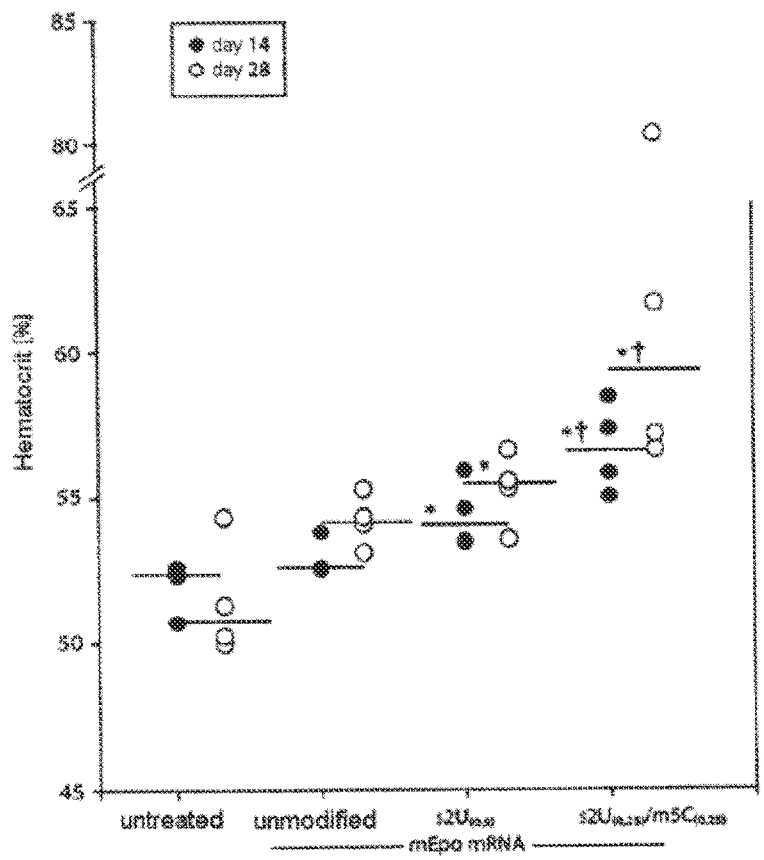

FIG. 11B shows hematocrit values 14 days and 28 days after administration of EPO-encoding mRNA with different modifications. The diagram clearly shows that mice treated with mRNA modified according to the invention have a considerably higher hematocrit value.

Figure 11C:
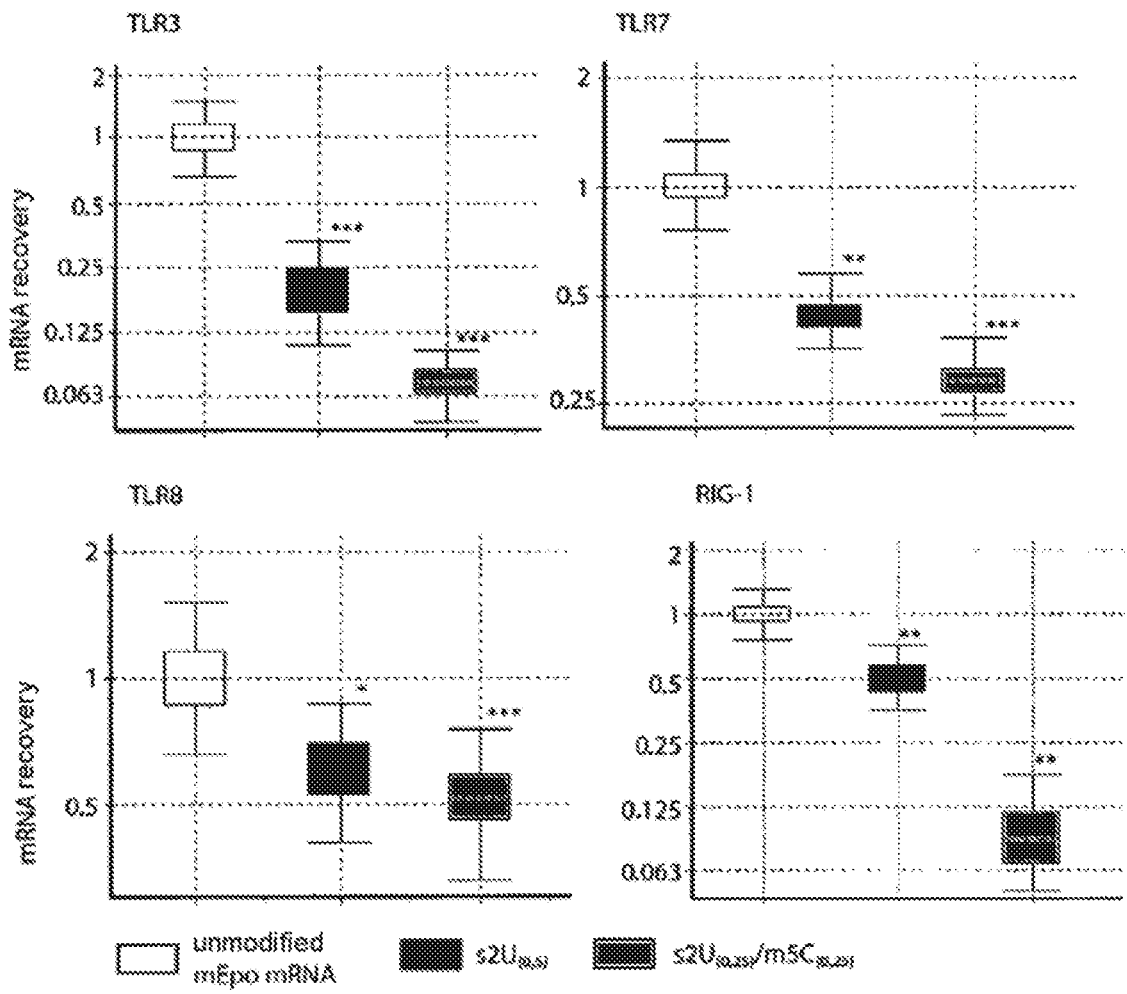

In the diagrams of FIG. 11C the production of the factors typical for an immunological reaction is plotted. It is found that all four inflammatory markers are elevated with the administration of unmodified mRNA, while with RNA modified according to the invention an immunological reaction is hardly detectable.

Figure 11D:
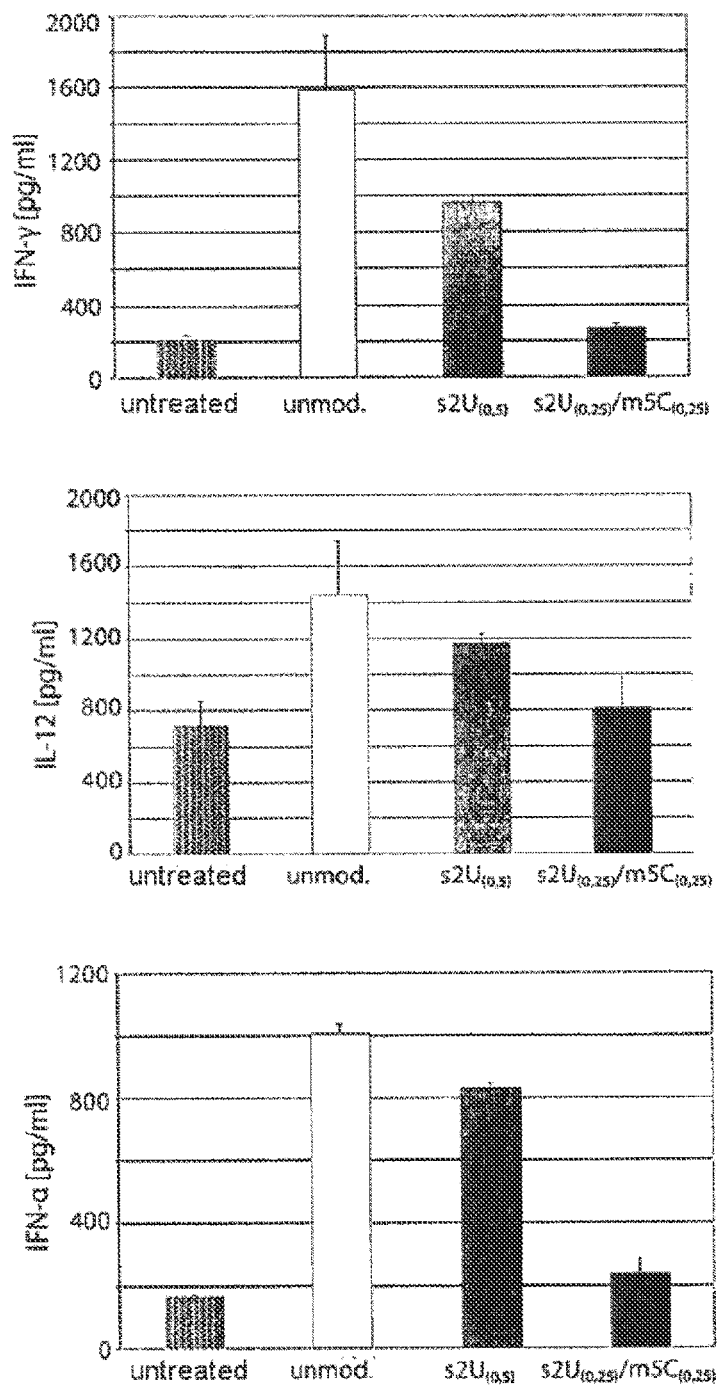

The diagrams of FIG. 11D show the corresponding values for IFN-α and IL-12, which are also inflammatory markers. Here also it is found that mRNA modified according to the invention causes practically no immunological reaction, in contrast to unmodified mRNA.

Figure 12:
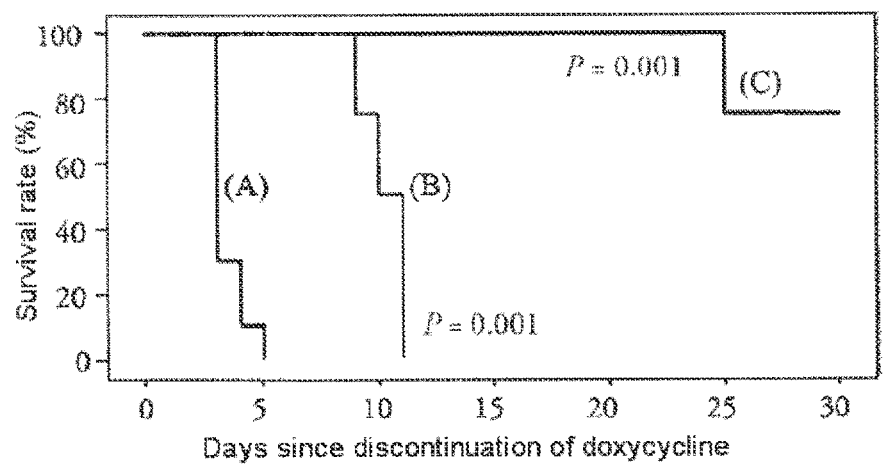

FIG. 12 shows a diagram in which the survival rate of three groups of mice which were given SP-B mRNA modified according to the invention twice in one week (B) or twice a week for 28 days (C), or in the comparison group modified EGFPLuc mRNA (A) is plotted. It is found that the mice only survive as long as they are given SP-B mRNA (B, C). Without provision of SP-B mRNA, the mice die (A).

Figure 13:
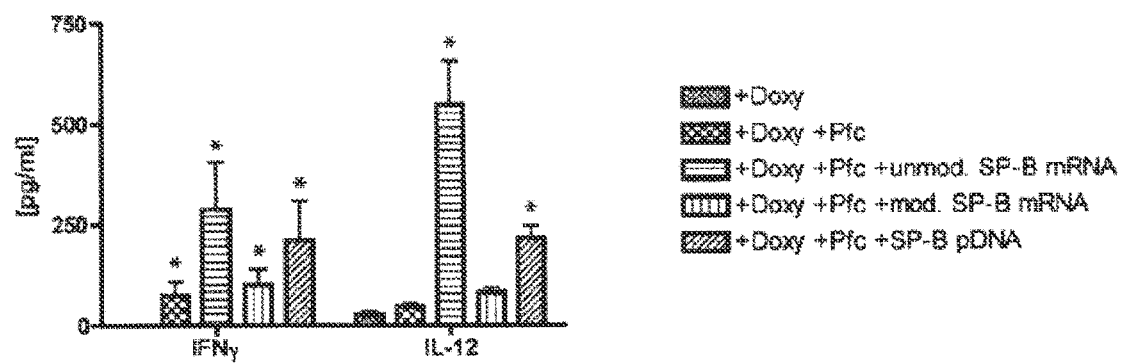

FIG. 13 shows cytokine levels in the bronchioalveolar lavage of mice 8 hours after administration of unmodified SP-B mRNA, SP-B mRNA modified according to the invention or SP-B plasmid DNA. The results show that in contrast to the intratracheal administration of unmodified mRNA or plasmid DNA, which each lead to a marked rise in the inflammatory markers IFNγ and IL-12, on administration of SP-B mRNA modified according to the invention the inflammatory markers are practically not elevated compared to the untreated group or to the group treated with perfluorocarbon.

Figure 14:
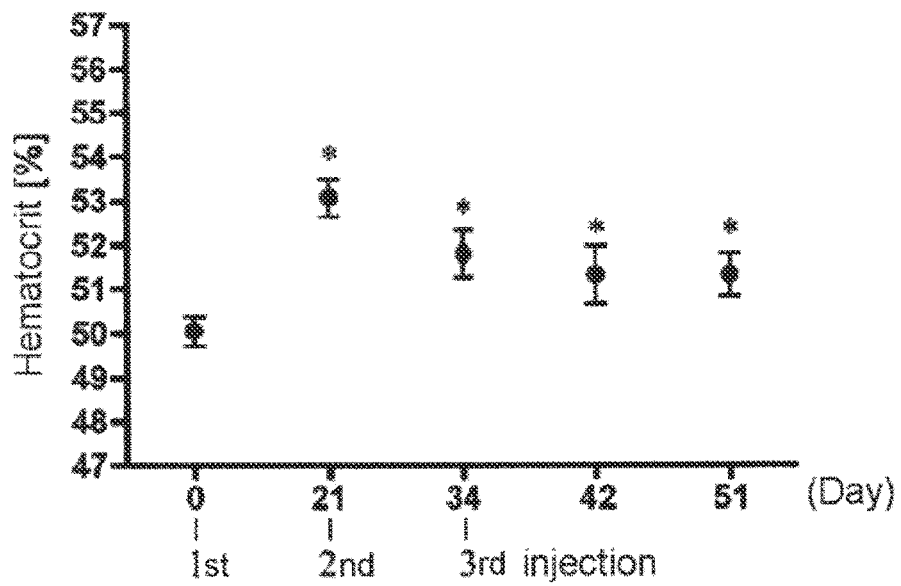

FIG. 14 shows hematocrit values as obtained after repeated administration of mEPO mRNA modified according to the invention. The results show that the repeated administration of mEPO mRNA modified according to the invention is well tolerated and results in long-persisting elevation of the hematocrit.

Figure 15:
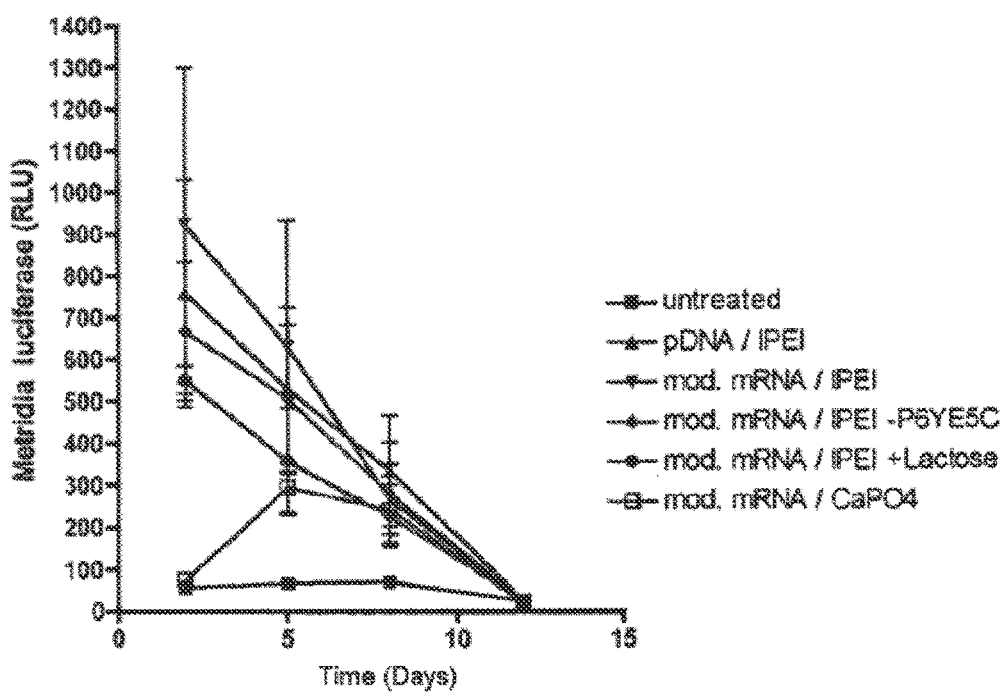

FIG. 15 shows the luciferase expression of cells which were incubated with titanium implants which were provided with coatings containing different forms of RNA modified according to the invention. It was found that RNA modified according to the invention which was contained in a coating of delayed release polymer which had been applied onto titanium plates and which was gradually released therefrom did not lose its activity.

Figure 16:
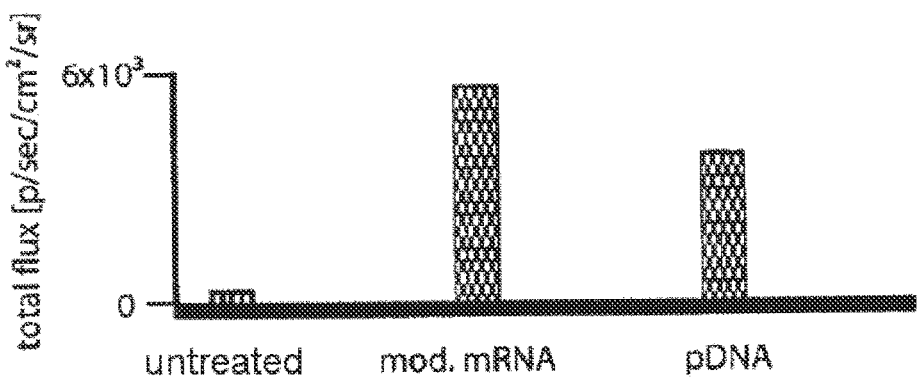

FIG. 16 shows the luciferase expression for coatings applied onto titanium implants which contained modified mRNA. It was found that the protein expression for mRNA modified according to the invention was far higher than for untreated RNA, but was also higher than for plasmid DNA.

Figure 17A:
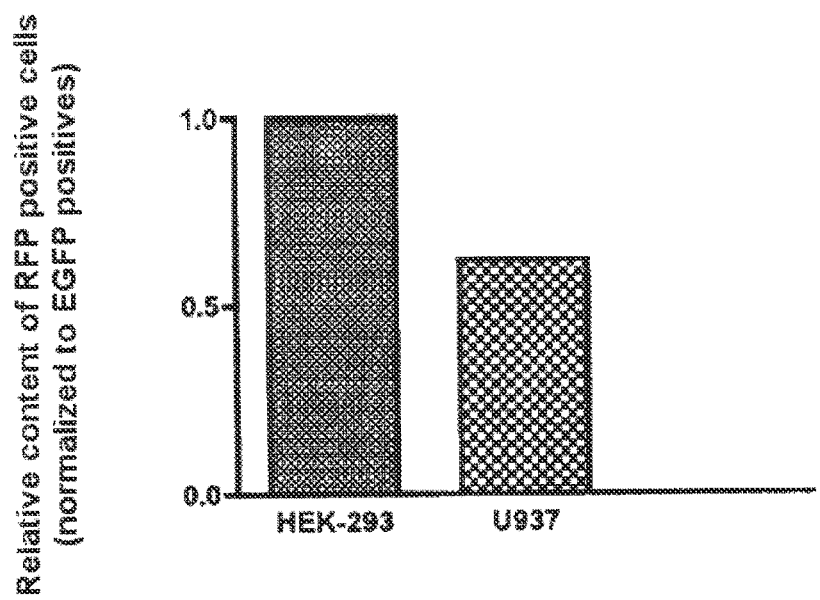

FIGS. 17A and 17B respectively show the relative content of RFP-positive cells and the relative RFP expression of mRNA which has micro-RNA binding sites for micro-RNA 142-3p. It was found that the content of RFP-positive cells for RNA having micro-RNA binding sites was lower and the expression of the encoded protein was considerably lower in the cells which contained the corresponding micro-RNA 142-3p.

FIG. 18 shows the sequence of an RNA modified by incorporation of micro-RNA binding sites, which encodes RFP. The RFP sequence is shown with a gray background. The fourfold tandem repetition of the micro-RNA binding site for the micro-RNA 142-3p (with light gray background) with the spacing sequences (no background) is underlined.

According to the invention, a polyribonucleotide molecule with partially multiply modified nucleotides, a partially multiply modified mRNA, an IVT mRNA, and the use of the RNA molecules for the production of a drug for the treatment of diseases due to deficient or defective genes or for the treatment of diseases which can be moderated or cured by the provision of proteins in vivo, such as factors, stimulators, inducers or enzymes, are provided. In a further embodiment, the mRNA according to the invention is combined with target binding sites, targeting sequences and/or with micro-RNA binding sites, in order to allow activity of the desired mRNA only in the relevant cells. In a further embodiment, the RNA according to the invention is combined with micro-RNAs or shRNAs downstream of the 3' polyA tail. In a further embodiment, RNA whose duration of action has been adjusted or extended by further specific modifications is provided.

Thus a subject of the invention is an RNA with increased stability and decreased immunogenicity. The RNA according to the invention can be made in a manner known per se. As a rule it is made by transcription of a DNA which encodes the intact or desired protein which can influence an illness or the lack or deficient form whereof causes a disease.

In the context of the present invention, RNA should be understood to mean any polyribonucleotide molecule which, if it comes into the cell, is suitable for the expression of a protein or fragment thereof or is translatable to a protein or fragment thereof. The term "protein" here encompasses any kind of amino acid sequence, i.e. chains of two or more amino acids which are each linked via peptide bonds and also includes peptides and fusion proteins.

The RNA according to the invention contains a ribonucleotide sequence which encodes a protein or fragment thereof whose function in the cell or in the vicinity of the cell is needed or beneficial, e.g. a protein the lack or defective form whereof is a trigger for a disease or an illness, provision whereof can moderate or prevent a disease or an illness, or a protein which can promote a process which is beneficial for the body, in a cell or its vicinity. As a rule, the RNA according to the invention contains the sequence for the complete protein or a functional variant thereof. Further, the ribonucleotide sequence can encode a protein which acts as a factor, inducer, regulator, stimulator or enzyme, or a functional fragment thereof, where this protein is one whose function is necessary in order to remedy a disorder, in particular a metabolic disorder or in order to initiate processes in vivo such as the formation of new blood vessels, tissues, etc. Here, functional variant is understood to mean a fragment which in the cell can undertake the function of the protein whose function in the cell is needed or the lack or defective form whereof is pathogenic. In addition, the RNA according to the invention can also have further functional regions and/or 3' or 5' noncoding regions. The 3' and/or 5' noncoding regions can be the regions naturally flanking the encoded protein or else artificial sequences which contribute to the stabilization of the RNA. Those skilled in the art can discover the sequences suitable for this in each case by routine experiments.

In a preferred embodiment, the RNA contains an m7GpppG cap, an internal ribosome entry site (IRES) and/or a polyA tail at the 3' end in particular in order to improve translation. The RNA can have further regions promoting translation. Critical for the RNA according to the invention is its content of modified nucleotides.

An RNA according to the invention with increased stability and diminished immunogenicity is obtained by using for the production thereof a nucleotide mixture wherein the content of the modified cytidine nucleotides and the modified uridine nucleotides is set. The RNA according to the invention is preferably produced with a nucleotide mixture which contains both unmodified and also modified nucleotides, where 5 to 50% of the cytidine nucleotides and 5 to 50% of the uridine nucleotides are modified. The adenosine- and guanosine-containing nucleotides can be unmodified. A nucleotide mixture can also be used wherein some of the ATPs and/or GTPs are also modified, where their content should not exceed 20% and where their content, if present, should preferably lie in a range from 0.5 to 10%.

Hence in a preferred embodiment an mRNA is provided which has 5 to 50% of modified cytidine nucleotides and 5 to 50% of uridine nucleotides and 50 to 95% of unmodified cytidine nucleotides and 50 to 95% of unmodified uridine nucleotides, and the adenosine and guanosine nucleotides can be unmodified or partially modified, and they are preferably present in unmodified form.

Preferably 10 to 35% of the cytidine and uridine nucleotides are modified and particularly preferably the content of the modified cytidine nucleotides lies in a range from 7.5 to 25% and the content of the modified uridine nucleotides in a range from 7.5 to 25%. It has been found that in fact a relatively low content, e.g. only 10% each, of modified cytidine and uridine nucleotides can achieve the desired properties, under the precondition that these are the modifications according to the invention.

The nature of the modification of the nucleosides has an effect on the stability and hence the lifetime and biological activity of the mRNA. Suitable modifications are set out in the following table:

| Name | Base modification (5-position) | Sugar modification (2'-position) | Naturally in mRNA |
|---|---|---|---|
| Uridine | | | |
| 5-methyluridine 5''-triphosphate (m5U) | $CH_3$ | — | no |
| 5-iodouridine 5'-triphosphate (I5U) | I | — | no |
| 5-bromouridine 5'-triphosphate (Br5U) | Br | — | no |
| 2-thiouridine 5'-triphosphate (S4U) | S (in 2 position) | — | no |
| 4-thiouridine 5'-triphosphate (S2U) | S (in 4 position) | — | no |
| 2'-methyl-2'-deoxyuridine 5'-triphosphate (U2'm) | — | $CH_3$ | yes |
| 2'-amino-2'-deoxyuridine 5'-triphosphate (U2'NH2) | — | $NH_2$ | no |
| 2'-azido-2'-deoxyuridine 5'-triphosphate (U2'N3) | — | $N_3$ | no |
| 2'-fluoro-2'-deoxyuridine 5'-triphosphate (U2'F) | — | F | no |
| Cytidine | | | |
| 5-methylcytidine 5'-triphosphate (m5C) | $CH_3$ | — | yes |
| 5-iodocytidine 5'-triphosphate (I5U) | I | — | no |
| 5-bromocytidine 5'-triphosphate (Br5U) | Br | — | no |
| 2-thiocytidine 5'-triphosphate (S2C) | S (in 2 position) | — | no |
| 2'-methyl-2'-deoxycytidine 5'-triphosphate (C2'm) | — | $CH_3$ | yes |
| 2'-amino-2'-deoxycytidine 5'-triphosphate (C2'NH2) | — | $NH_2$ | no |
| 2'-azido-2'-deoxycytidine 5'-triphosphate (C2'N3) | — | $N_3$ | no |
| 2'-fluoro-2'-deoxycytidine 5'-triphosphate (C2'F) | — | F | no |

-continued

| Name | Base modification (5-position) | Sugar modification (2'-position) | Naturally in mRNA |
|---|---|---|---|
| Adenosine | | | |
| N6-methyladenosine 5'-triphosphate (m6A) | CH₃ (in 6 position) | — | yes |
| N1-methyladenosine 5'-triphosphate (m1A) | CH₃ (in 1 position) | — | no |
| 2'-O-methyladenosine 5'-triphosphate (A2'm) | — | CH₃ | yes |
| 2'-amino-2'-deoxyadenosine 5'-triphosphate (A2'NH2) | — | NH₂ | no |
| 2'-azido-2'-deoxyadenosine 5'-triphosphate (A2'N3) | — | N₃ | no |
| 2'-fluoro-2'-deoxyadenosine 5'-triphosphate (A2'F) | — | F | no |
| Guanosine | | | |
| N1-methylguanosine 5'-triphosphate (m1G) | CH₃ (in 1 position) | — | no |
| 2'-O-methylguanosine 5'-triphosphate (G2'm) | — | CH₃ | yes |
| 2'-amino-2'-deoxyguanosine 5'-triphosphate (G2'NH2) | — | NH₂ | no |
| 2'-azido-2'-deoxyguanosine 5'-triphosphate (G2'N3) | — | N₃ | no |
| 2'-fluoro-2'-deoxyguanosine 5'-triphosphate (G2'F) | — | F | no |

For the RNA according to the invention, either all uridine nucleotides and cytidine nucleotides can each be modified in the same form or else a mixture of modified nucleotides can be used for each. The modified nucleotides can have naturally or not naturally occurring modifications. A mixture of various modified nucleotides can be used. Thus for example one part of the modified nucleotides can have natural modifications, while another part has modifications not occurring naturally or a mixture of naturally occurring modified and/or not naturally occurring modified nucleotides can be used. Also, a part of the modified nucleotides can have a base modification and another part a sugar modification. In the same way, it is possible that all modifications are base modifications or all modifications are sugar modifications or any suitable mixture thereof. By variation of the modifications, the stability and/or duration of action of the RNA according to the invention can be selectively adjusted.

In one embodiment of the invention, at least two different modifications are used for one type of nucleotide, where one type of the modified nucleotides has a functional group via which further groups can be attached. Nucleotides with different functional groups can also be used, in order to provide binding sites for the attachment of different groups. Thus for example a part of the modified nucleotides can bear an azido group, an amino group, a hydroxy group, a thiol group or some other reactive group which is suitable for reaction under predefined conditions. The functional group can also be such that it can under certain conditions activate a naturally present group capable of binding, so that molecules with functions can be coupled. Nucleotides which are modified so that they provide binding sites can also be introduced as adenosine or guanosine modifications. The selection of the particular suitable modifications and the selection of the binding sites to be made available depends on what groups are to be introduced and with what frequency these are to be present. Thus the content of the nucleotides provided with functional and/or activating groups depends on how high the content of groups to be coupled is to be and can easily be determined by those skilled in the art. As a rule, the content of nucleotides modified with functional and/or activating groups, if present, is 1 to 25% of the modified nucleotides. Those skilled in the art can if necessary determine the most suitable groups in each case and the optimal content thereof by routine experiments.

It has been found that particularly good results can be achieved when the RNA according to the invention 2'-thio-uridine as a modified uridine-containing nucleotide. Furthermore, it is preferred that the RNA according to the invention contains 5'-methylcytidine as a modified cytidine nucleotide. These two nucleotides are therefore preferred. Also preferred is a combination of these two modifications. In an especially preferred embodiment, these two nucleotides are each present at a content of 10 to 30%. Nucleotides modified in another way can optionally also be present, as long as the total content of modified nucleotides does not exceed 50% of the particular nucleotide type.

Preferred is a polyribonucleotide wherein 5 to 50%, particularly preferably 5 to 30% and in particular 7.5 to 25% of the uridine nucleotides are 2'-thiouridine nucleotides, and 5 to 50%, particularly preferably 5 to 30% and in particular 7.5 to 25% of the cytidine nucleotides are 5'-methylcytidine nucleotides, where the adenosine and guanosine nucleotides can be unmodified or partially modified nucleotides. In a preferred embodiment, this mRNA according to the invention additionally has a 7'-methylguanosine cap and/or a poly(A) end. Thus in a preferred embodiment the mRNA is produced in its mature form, i.e. with a GppG cap, an IRES and/or a polyA tail.

The optimal types and contents of modified uridine nucleotides and cytidine nucleotides for a specific RNA can be determined with routine experiments. In this context an mRNA whose immunogenicity is so low that the treated organism is not stressed and which has a predetermined stability and hence predetermined duration of expression is described as optimal. Methods for the testing and determination of these properties are known to those skilled in the art and are described below and in the examples.

The RNA according to the invention can be produced in a manner known per se. A method wherein the mRNA according to the invention is produced by in vitro transcription from a mixture of ATP, CTP, GTP and UTP, wherein 5 to 50%, preferably 5 to 30% and in particular 7.5 to 25% of the cytidine nucleotides and 5 to 50%, preferably 5 to 30% and in particular 7.5 to 25% of the uridine nucleotides are modified and the rest is unmodified is for example suitable. Guanosine and adenosine nucleosides, in particular adenosine, can optionally also be modified. However, the modification of UTP and CTP in the stated range is essential for the invention. If the content of modified UTP and/or modified CTP is lower or higher, the advantageous properties are no longer achieved. Thus it has been found that outside the claimed ranges the mRNA is no longer so stable. Moreover, with a lower content of modification immunological reactions are to be expected. In order to set the suitable ratio of unmodified and modified nucleotides, the RNA is appropriately made using a nucleotide mixture, the nucleoside contents whereof are partly modified and partly unmodified in accordance with the desired ratio, where according to the invention at least 5% of the uridine nucleosides and at least 5% of the cytidine nucleosides are modified, but in total not more than 50% of uridine nucleosides and cytidine nucleosides respectively are modified. Further nucleosides, i.e. adenosine and guanosine, can be modified, however an upper limit of 50% modification, preferably 20%, should also not be exceeded for these nucleosides. Preferably only the appropriate contents of the uridine nucleosides and cytidine nucleosides are modified.

The nucleosides to be modified can have modifications such as are also to be found in naturally occurring nucleosides, e.g. methylations or binding variations, but also "synthetic", i.e. not occurring in nature, modifications or a mixture of nucleosides with natural and/or synthetic modifications can be used. Thus naturally modified nucleosides of at least one type can be combined with synthetically modified nucleosides of the same type or another type or else naturally and synthetically modified nucleosides of one type with only naturally, only synthetically or mixed naturally/synthetically modified nucleosides of another type, where "type" here refers to the type of the nucleosides, i.e. ATP, GTP, CTP or UTP. In many cases, as stated above, for the improvement of immunogenicity and stability or for adjustment of properties it can be beneficial to combine modified nucleosides with functional groups, which provide binding sites, with non-functionally modified nucleosides. The most suitable type or combination can easily be found by those skilled in the art by routine experiments such as are for example also stated below. Particularly preferably, 2-thiouridine and 5-methylcytidine are used as modified nucleosides. If functionally modified nucleosides are desired, 2'-azido and 2'-amino nucleosides are preferably considered.

The length of the mRNA used according to the invention depends on the gene product or protein or protein fragment which is to be provided or supplemented. Hence the mRNA can be very short, e.g. have only 20 or 30 nucleotides, or else corresponding to the length of the gene have several thousand nucleotides. Those skilled in the art can select the suitable sequence each time in the usual way.

What is essential is that the function of the protein causing a disease, of the protein moderating or preventing a disease or of the protein controlling a beneficial property, for which the mRNA is to be used, can be provided.

2'-Thiouridine is preferably used as the modified uridine-containing nucleotide for the production of the RNA according to the invention. Furthermore, it is preferable to use 5'-methylcytidine as the modified cytidine nucleotide. Hence for the production of the RNA according to the invention a nucleotide mixture which as well as ATP and GTP respectively contains 95 to 50% of unmodified CTP and 95 to 50% of unmodified UTP and 5 to 50% of 2'-thiouridine nucleotides and 5 to 50% of methylcytidine nucleotides is preferably used. Hence a polyribonucleotide wherein 5 to 50%, preferably 5 to 30% and in particular 7.5 to 25% of the uridine nucleotides are 2'-thiouridine nucleotides and 5 to 50%, preferably 5 to 30% and in particular 7.5 to 25% of the cytidine nucleotides are 5'-methylcytidine nucleotides and the adenosine and guanosine nucleotides are unmodified nucleotides is particularly preferred. Such a combination leads to the production of a partially modified RNA which is characterized by particularly high stability. It could be shown that RNA which was produced with a nucleotide mixture which as CTP and UTP contained 5 to 50% of 2-thiouridine and 5-methylcytidine nucleotides respectively is especially stable, i.e. had a lifetime increased up to 10-fold compared to unmodified RNA or RNA modified in known manner.

In a further preferred embodiment, 1 to 50%, preferably 2 to 25%, of the 5 to 50% modified uridine or cytidine nucleotides are nucleotides which have binding site-creating or activating groups as a modification, i.e. 0.5 to 20%, preferably 1 to 10% of the cytidine nucleotides and/or uridine nucleotides can have a modification which creates a binding site, such as for example azido, NH, SH or OH groups. Through this combination, an RNA which is both particularly stable and also versatile is provided.

Further, it is preferred that the polyribonucleotide molecule built up of unmodified and modified nucleotides has a 7'-methylguanosine cap and/or a poly(A) end. In addition, the RNA can also have additional sequences, e.g. non-translated regions and functional nucleic acids, such as are well known to those skilled in the art.

The RNA according to the invention is preferably provided as in vitro transcribed RNA (IVT RNA). The materials necessary for performing the in vitro transcription are known to those skilled in the art and available commercially, in particular buffers, enzymes and nucleotide mixtures. The nature of the DNA used for the production of the RNA according to the invention is also not critical; as a rule it is cloned DNA.

As stated above, an RNA, in particular mRNA, which has a predetermined content of modified uridine nucleosides and modified cytidine nucleosides is provided. The optimal content of modified uridine nucleosides and cytidine nucleosides for a specific mRNA can be determined by routine experiments which are well known to those skilled in the art.

The RNA according to the invention is preferably used for the therapy of diseases or for the provision of proteins beneficial to the body. When the RNA according to the invention is used for the therapy of diseases, it preferably has the in vitro transcript for a protein or protein fragment, a defect or lack whereof leads to a disease condition or the provision whereof leads to the moderation of an illness. For the production of the RNA according to the invention, a DNA is preferably used which encodes a protein or protein fragment, a defect or lack whereof leads to a disease or is connected with an illness. In one embodiment, the DNA of a gene, a defect or lack whereof leads to a disease or illness, is used for the production of the RNA according to the invention. In another embodiment, a DNA which encodes a protein the presence, perhaps temporary, whereof is beneficial or curative for an organism is used for the production of the RNA according to the invention. Here any state wherein physical and/or mental/psychological disorders or changes are subjectively and/or objectively present, or where the abnormal course of physical, mental or psychological processes makes medical care necessary and may lead to inability to work is regarded as a disease or illness.

Here a protein or protein fragment the presence whereof can moderate an illness or be beneficial or supportive to the body are understood to mean proteins or protein fragments which, without a genetic defect being present, are to be made fully or temporarily available to the body since they are missing either because of disorders of some kind or because of natural circumstances or because they can benefit the body under certain conditions, e.g. in the treatment of defects or in the context of implantation. These also include altered forms of proteins or protein fragments, i.e. forms of proteins which alter in the course of the metabolism, e.g. matured forms of a protein, etc. Proteins which play a part in growth processes and angiogenesis, which are for example necessary in controlled regeneration and can then be formed specifically by introduction of the mRNA according to the invention, can also be provided. This can for example be useful in growth processes or for the treatment of bone defects, tissue defects and in the context of implantation and transplantation.

It has been found that the mRNA modified according to the invention can advantageously be used in order to promote the ingrowth of implanted prostheses. If it is available on the surface of prostheses to be inserted such as tooth implants, hip endoprostheses, knee endoprostheses or vertebral fusion bodies, the mRNA according to the invention can release factors which can promote the ingrowth, new formation of blood vessels and other functions which are necessary for the newly inserted prostheses. Thus for example the administration of biologically active substances such as growth factors such as BMP-2 or angiogenesis factors in the context of implantation of prostheses or thereafter is known. Since biological substances very often have extremely short half-lives, it was previously necessary to use very high dosages, which burdens the patient with severe side effects. According to the invention, this disadvantage is avoided since using the RNA according to the invention the desired and/or needed proteins can be used selectively and suitably dosed. This decreases or even completely spares the patient the side effects. In this embodiment, the RNA according to the invention which encodes desired and/or needed substances such as growth factors, angiogenesis factors etc. can be applied onto the implant in a coating releasing the RNA in a measured manner and then released gradually therefrom in a measured manner, so that the cells in the vicinity of the implant can continuously or intermittently produce and if necessary release the desired factors. Carriers, as a rule biocompatible, synthetic, natural or mixed natural-synthetic polymers, the release properties whereof can be specifically adjusted, are well known and thus need no more detailed explanation here. Polylactide or polylactide/glycolide polymers are for example used. In this way it is possible selectively to release the desired factors continuously, intermittently, over a longer or shorter time and at the desired site.

In the context of the present invention, a deficient or defective gene or deficiency or lack are understood to mean genes which are not expressed, incorrectly expressed or not expressed in adequate quantity and as a result cause diseases or illnesses, e.g. by causing metabolic disorders.

The RNA according to the invention can appropriately be used in any case where a protein, which would naturally be present in the body but is not present or is present in deficient form or in too small a quantity because of gene defects or diseases, is to be provided to the body. Proteins and the genes encoding them, the deficiency or defect whereof are linked with a disease, are known. Various proteins and genes in case of a lack whereof the RNA according to the invention can be used are listed below.

TABLE 2

Diseases for which the administration of mRNA according to the invention can be indicated:

| Organ | Defect |
|---|---|
| Lung | surfactant protein B deficiency |
| Lung | ABCA3 deficiency |
| Lung | cystic fibrosis |
| Lung | alpha-1 antitrypsin deficiency |

TABLE 2-continued

Diseases for which the administration of mRNA according to the invention can be indicated:

| | |
|---|---|
| Plasma proteins | clotting defects such as hemophilia A and B |
| Plasma proteins | complement defects such as protein C deficiency |
| Plasma proteins | thrombotic thrombocytopenic purpura (TPP, ADAMTS 13 deficiency) |
| Plasma proteins | congenital hemochromatoses (e.g. hepcidin deficiency) |

Severe combined immunodeficiencies (SCID) (T, B and NK cells)
X-chromosomally inherited combined immunodeficiencies (X-SCID)
ADA-SCID (SCID due to lack of adenosine deaminase)
SCID with RAG1 mutation
SCID with RAG2 mutation
SCID with JAK3 mutation
SCID with IL7R mutation
SCID with CD45 mutation
SCID with CD3δ mutation
SCID with CD3ε mutation
SCID with purine nucleoside phosphorylase deficiency (PNP deficiency)

| Disease | Defect or mutation |
|---|---|
| Septic granulomatoses (granulocytes) | |
| X-chromosomal recessive CGD | mutation of the gp91-phox gene |
| CGD cytochrome b positive type 1 | mutation of the p47-phox gene |
| CGD cytochrome b positive type 2 | mutation of the p67-phox gene |
| CGD cytochrome b negative | mutation of the p22-phox gene |
| Other storage diseases | |
| mutation in the glucocerebrosidase gene | Gaucher's disease |
| mutation in the GALC gene | Krabbe's disease |
| lysosomal storage diseases | mucopolysaccharidoses |

| Type | Defect | Specific name |
|---|---|---|
| Glycogen storage diseases | | |
| I (a-d) | Ia: glucose-6-phosphatase Ib, Ic, Id: glucose-6-phosphate translocase | Von Gierke's disease |
| II | lysosomal α-glucosidase | Pompe's disease |
| III | glycogen debranching enzyme | Cori's disease |
| IV | 1,4-α-glucan branching enzyme | Andersen's disease |
| V | muscle glycogen phosphorylase | McArdle's disease |
| VI | glycogen phosphorylase/ phosphorylase kinase system (liver and muscle) | Hers disease |
| VII | phosphofructokinase (muscle) | Tarui's disease |
| VIII | liver phosphorylase | |
| IX (a-c) | liver phosphorylase | |
| X | cAMP-act. phosphorylase | |
| XI | GLUT-2 defect | Fanconi-Bickel syndrome |
| 0 | UDP glycogen synthase | |
| Other storage diseases | | |
| mutation in the glucocerebrosidase gene | | Gaucher's disease |
| mutation in the GALC gene | | Krabbe's disease |
| lysosomal storage diseases | | mucopolysaccharidoses |

Other diseases based on defective genes are stated below:

| Type | Variant | | Clinical features | Defective enzyme |
|---|---|---|---|---|
| I-H | Hurler-Pfaundler syndrome | | dysmorphia (gargoylism), cognitive retardation, skeletal malformation (dysostosis), corneal clouding, decreased growth, hernias, hepatomegaly | α-L-iduronidase |
| I-S | Scheie's disease | | not mentally retarded, skeletal malformation (dysostosis), corneal clouding, heart valve faults | α-L-iduronidase |
| I-H/S | Hurler/Scheie variants | | mentally between I-H and I-S | α-L-iduronidase |
| II | Hunter's syndrome | | moderate cognitive retardation, skeletal malformation (dysostosis), considerable somatic changes, premature deafness | iduronate sulfate silfatase |
| III | Sanfilippo syndrome | type A | cognitive retardation, dysmorphia, corneal clouding can be lacking, frequently hearing impairment, rapid progression | heparan sulfate sulfamidase |
| | | type B | | α-N-acetylglucose amidase |
| | | type C | | acetyl-CoA; α-glucosaminid-N-acetyl transferase |
| | | type D | | N-acetylglucosamine-6-sulfate sulfatase |
| IV | Morquio syndrome | type A | normal cognitive development, skeletal malformation (dysostosis) very marked, no corneal clouding | N-acetylglucosamine-6-sulfate sulfatase |
| | | type B | mild form of type A | β-galactosidase |
| V | now: type I-S, see above | | | |
| VI | Maroteaux-Lasny syndrome | | normal cognitive development, severe skeletal malformation (dysostosis), corneal clouding, decreased growth | N-acetylgalactos-amine-4-sulfate sulfatase |
| VII | Sly syndrome | | moderate dysmorphia and skeletal malformations, corneal clouding, normal to limited intelligence | β-glucuronidase |

Thus the above table shows examples of genes in which a defect leads to a disease which can be treated by transcript replacement therapy with the RNA according to the invention. In particular here, hereditary diseases can be mentioned which for example affect the lungs, such as SPB deficiency, ABCA3 deficiency, cystic fibrosis and α1-antitrypsin deficiency, which affect plasma proteins and cause clotting defects and complement defects, immune defects such as for example SCID, septic granulomatosis and storage diseases. In all these diseases, a protein, e.g. an enzyme, is defective, which can be treated by treatment with the RNA according to the invention, which makes the protein encoded by the defective gene or a functional fragment thereof available.

Thus, examples of proteins which can be encoded by the RNA according to the invention are erythropoietin (EPO), growth hormone (somatotropin, hGH), cystic fibrosis transmembrane conductance regulator (CFTR), growth factors such as GM-SCF, G-CSF, MPS, protein C, hepcidin, ABCA3 and surfactant protein B. Further examples of diseases which can be treated with the RNA according to the invention are hemophilia A/B, Fabry's disease, CGD, ADAMTS13, Hurler's disease, X chromosome-mediated A-γ-globulinemia, adenosine deaminase-related immunodeficiency and respiratory distress syndrome in the newborn, which is linked with SP-B. Particularly preferably, the mRNA according to the invention contains the sequence for surfactant protein B (SP-B) or for erythropoietin. Further examples of proteins which can be encoded by RNA modified according to the invention are growth factors such as BMP-2 or angiogenesis factors.

A further use field for the RNA according to the invention arises for diseases or illnesses wherein proteins are no longer or not formed in the body, e.g. because of organ failure. At present, a recombinant protein is administered for replacement in such diseases. According to the invention, RNA is now provided for this so that the replacement of the missing protein can take place at the level of the transcript. This has several advantages. If the protein has glycosylations, then the replacement at the transcript level has the effect that the glycosylation typical in humans takes place in the body. With proteins that are recombinant, i.e. normally produced in microorganisms, the glycosylation is as a rule different from that in the body where replacement is to be effected. This can lead to side effects. Generally it can be assumed that the protein expressed from the RNA according to the invention is identical with the endogenous protein as regards structure and glycosylation, which is as a rule not the case with recombinant proteins.

Examples of proteins replacement or introduction whereof can be desirable are functional proteins such as erythropoietin and growth factors such as somatotropin (hGH), G-CSF, GM-CSF and thrombopoietin.

A further field in which the RNA according to the invention can be used is the field of regenerative medicine. Through disease processes or through aging, degenerative diseases arise which can be treated and moderated or even cured by introduction of proteins produced too little or not at all owing to the disease or aging processes. By introduction of the relevant RNA encoding these proteins, the degenerative process can be halted or regeneration can even be initiated. Examples of this are growth factors for tissue regeneration which can be used e.g. in growth disorders, in degenerative diseases such as osteoporosis, arthrosis or impaired wound healing. Here the RNA according to the invention offers not only the advantage that the missing protein can be provided selectively and in the correct dosage but in addition it is possible to provide the protein in a time window. Thus for example with impaired wound healing, the relevant healing factor or growth factor can be provided for a limited time by dosed administration of the RNA. In addition, via mechanisms to be explained later, it can be arranged that the RNA is selectively brought to the site of its desired action.

Examples of factors which can be expressed with the RNA according to the invention so as to have a regenerative action are fibroblast growth factor (FGF), e.g. FGF-1-23, transforming growth factor (TGF), e.g. TGF-α and TGF-β, BMPs (bone morphogenetic protein), e.g. BMP1 to 7, 8a & b, 10 & 15, platelet-derived growth factor (PDGF), e.g. PDGF-A, PDGF-B, PDGF-C and PDGF-D, epidermal growth factor (EGF), granulocyte-macrophage colony stimulating factor (GM-CSF), vascular endothelial growth factor (VEGF-A to F and PlGF), insulin-like growth factors, e.g. IgF1 and IgF2, hepatocyte growth factor (HGF), interleukins, e.g. interleukin-1B, IL-8 and IL-1 to 31, nerve growth factor (NGF) and other factors which stimulate the formation of erythrocytes, neutrophils, blood vessels, etc.

The RNA according to the invention can also be selectively used in the field of cancer diseases. Through the expression of tailor-made T cell receptors in T lymphocytes which recognize specific tumor-associated antigens, these can become still more effective. It has already been shown that in principle mRNA can be successfully used in this field. However until now its use was prevented by the immunogenic effects already described above. With the less immunogenic and highly stable RNA provided according to the invention, it is now possible to express T cell receptors appropriately.

RNA according to the invention can also be used to express transcription factors which ensure that somatic cells are reprogrammed into embryonic stem cells. Examples of this are O-cp3/4, Sox2, KLF4 and c-MYC. Stable RNA, especially mRNA, according to the invention which encodes these transcription factors can thus lead to the production of stem cells without creating the side effects which can occur with the previously considered gene transfer via viral or non-viral vectors.

An advantage of using the RNA according to the invention is that, in contrast to the use of DNA vectors, the duration of the treatment is adjustable. In the case of the induction of stem cells, it is as a rule desirable that the transcription factors are only transiently active, in order to reprogram somatic cells into stem cells. Through dosed administration of the relevant RNA encoding the transcription factors the activity is controllable over time. In contrast to this, with the previously known methods there is the danger of integration of the genes administered, which leads to complications, e.g. tumorigenesis, and moreover renders it impossible to control the duration.

In the vaccines field, the RNA according to the invention also offers new possibilities. The standard development of vaccines depends on killed or weakened pathogens. More recently, DNA which encodes a protein of the pathogen has also come under consideration. The production of these vaccines is laborious and very time-consuming. Often side effects arise and lead to vaccinations being refused. With the mRNA according to the invention, it is possible to provide a vaccine which does not have the problems associated with pathogens or DNA. In addition, such a vaccine can be produced very quickly as soon as the antigen sequences of a pathogen are known. This is particularly advantageous under the threat of pandemics. Thus in one embodiment of the present invention, an RNA is provided which encodes an antigenic part of a disease pathogen, e.g. a surface antigen. It is also possible to provide an mRNA which encodes an amino acid sequence which has a combination of several epitopes, optionally linked by spacer sections. A combination with immunomodulating substances is also possible, either through the RNA encoding a fusion protein or as a combination of nucleic acids.

Furthermore, the RNA according to the invention can also encode proteins which as factors, stimulators, inducers, etc. have an influence on the course of disease. Examples are diseases which are not directly attributable to a gene defect but wherein the disease process can be positively influenced by means of mRNA expression. Examples are: erythropoietin for stimulation of the formation of erythrocytes, G-CSF or GM-SCF for the formation of neutrophils, growth factors for the formation of new blood vessels, for bone and wound healing as factors for "tissue engineering", treatment of tumors by induction of apoptosis or by formation of proteinaceous cell poisons, e.g. diphtheria toxin A, by induction of pluripotent stem cells (iPS) etc.

It has been found that only a polyribonucleotide according to the invention, which has a predetermined content of modified and unmodified nucleotides, has low immunogenicity with at the same time high stability. In order to be able to determine the optimal combination of modified and unmodified nucleotides for a certain polyribonucleotide, immunogenicity and stability can be determined in a manner known per se. For the determination of the immunogenicity of an RNA, various methods well known to those skilled in the art can be used. A very suitable method is the determination of inflammatory markers in cells as a reaction to the administration of RNA. Such a method is described in the examples. Cytokines which are associated with inflammation, such as for example TNF-α, IFN-α, IFN-β, IL-8, IL-6, IL-12 or other cytokines known to those skilled in the art are normally measured. The expression of DC activation markers can also be used for the estimation of immunogenicity. A further indication of an immunological reaction is the detection of binding to the Toll-like receptors TLR-3, TLR-7 and TLR-8 and to helicase RIG-1.

The immunogenicity is as a rule determined in relation to a control. In a common method, either the RNA according to the invention or an RNA that is unmodified or modified in another way is administered to cells and the secretion of inflammatory markers in a defined time interval as a reaction to the administration of the RNA is measured. As the standard used for comparison, either unmodified RNA can be used, in which case the immune response should be lower, or RNA which is known to cause little or no immune response, in which case the immune response to the RNA according to the invention should then lie in the same range and not be elevated. With the RNA according to the invention it is possible to lower the immune response compared to unmodified RNA by at least 30%, as a rule at least 50% or even 75% or even to prevent it completely.

The immunogenicity can be determined by measurement of the aforesaid factors, in particular by measurement of the TNF-α and IL-8 levels and the binding capacity to TLR-3, TLR-7, TLR-8 and helicase RIG-1. In order thereby to establish whether an mRNA has the desired low immunogenicity, the quantity of one or more of the aforesaid factors after administration of the polyribonucleotide concerned can be measured. Thus for example a quantity of the mRNA to be tested can be administered to mice via the caudal vein or i.p. and then one or more of the aforesaid factors can be measured in the blood after a predefined period, e.g. after 7 or 14 days. The quantity of factor is then related to the quantity of factor which is present in the blood of untreated animals. For the determination of the immunogenicity it has been found very valuable to determine the binding capacity to TLR-3, TLR-7, TLR-8 and/or helicase RIG-1. The TNF-α levels and IL-8 levels also provide very good indications. With the mRNA according to the invention, it is possible to lower the binding capacity to TLR-3, TLR-7, TLR-8 and RIG-1 by at least 50% compared to unmodified RNA. As a rule it is possible to lower the binding to said factors by at least 75% or even by 80%. In preferred embodiments, the binding capacity to TLR-3, TLR-7, TLR-8 and RIG-1 lies in the same range for the mRNA according to the invention and for animals to which no mRNA was administered. In other words, the mRNA according to the invention causes practically no inflammatory or immunological reactions.

In every case, the RNA according to the invention has such low immunogenicity that the general condition of the patient is not affected. A slight increase in the aforesaid factors can thus be tolerated as long as the general condition does not worsen as a result. Further properties of the mRNA according to the invention are its efficiency and stability. For this, transcription efficiency, transfection efficiency, translation efficiency and duration of protein expression are important and can be determined by methods known per se.

The transcription efficiency indicates how efficiently RNA can be produced from DNA. Here problems can arise with the use of a high content of modified nucleotides. The RNA modified according to the invention can be produced with high transcription efficiency.

In order to obtain stable and adequate expression of the proteins encoded by the RNA, it is important that sufficient RNA reaches the desired cells. This can be determined in that after administration of labeled RNA the content of RNA which has reached the cells is determined by measurement of the labeling. Flow cytometry can be used for the determination of the labeling. When labeling is effected with a fluorescent molecule, the transfection efficiency can be calculated, for example as the percentage of the cell population wherein the fluorescence intensity is higher compared to control cells which were only treated with PBS. It has been found that the RNA modified according to the invention can be produced effectively, in contrast to RNA wherein two or more nucleotide types have been 100% replaced by modified nucleotides, and that the transfection efficiency for RNA according to the invention, wherein only a part of the nucleotides is modified, is far higher than with RNA wherein any one type of nucleotides is 100% modified.

The translation efficiency designates the efficiency with which the RNA is translated into the protein. The higher the translation efficiency, the lower can be the dose of RNA that then has to be used for the treatment. The translation efficiency can be determined by comparing the proportion of translation for RNA modified according to the invention with the translation ratio for unmodified RNA. As a rule, the translation efficiency with the RNA according to the invention is somewhat lower than with unmodified RNA. This is however more than compensated by the far higher stability which is manifested in the duration of the protein expression.

The RNA according to the invention in particular provides for high stability, which results in long-continuing protein expression. Particularly when the RNA modified according to the invention is intended for the treatment of diseases due to gene defects, the longer it remains in the cell the more valuable it is. The more rapidly the RNA is degraded, the more rapidly the protein expression ends and the more often the RNA must be administered. Conversely, with a stable RNA which remains in the cell for a long time the frequency of dosing can be greatly reduced. It has been found that RNA modified according to the invention is stably expressed for up to 4 weeks.

For other embodiments, i.e. when RNA is only intended for temporary expression, the duration of the protein expression can be adjusted by influencing the stability.

A further valuable property of the RNA according to the invention is thus that the duration of action can be adjusted selectively via the stability so that the duration of the protein expression can be tailored so that it takes place in a desired time window. Secondly, a very long-acting RNA can be used where this is necessary. The RNA modified according to the invention, expression whereof can last up to 4 weeks, is thus ideally suited for the treatment of chronic diseases since here it only has to be given every 4 weeks. For embodiments wherein the RNA encodes factors which are to be supplied to the body over a prolonged period in order to moderate or prevent diseases, the high stability and long-lasting protein expression is also advantageous, e.g. for the use of RNA encoding erythropoietin. The RNA according to the invention can also especially advantageously be used for the treatment of hemophilia. Here it was previously necessary to administer the missing factor weekly. With the provision of the RNA according to the invention, the frequency of administration can be reduced, so that RNA encoding the factor now only has to be given every 2 or even every 4 weeks.

The stability of the mRNA according to the invention can be determined by methods known per se. Particularly suitable are methods for the determination of the viability of cells which contain RNA modified according to the invention in comparison to cells which contain unmodified or fully modified RNA, e.g. in comparison to RNA that is unmodified or modified in known manner. The production of the encoded protein over time can also be monitored. Here stability of an RNA is understood to mean that when it has been introduced into the cell, the RNA which can express the desired protein or is translatable into the protein or a functional fragment thereof, remains capable of expression over a prolonged period, is not immediately degraded and is not inactivated.

A method for testing the stability and the survival time of RNA in a cell thus consists in determining how long a protein encoded by the RNA is detectable in the cell or performs its function. Methods for this are described in the examples. Thus for example an mRNA with a sequence encoding a reporter molecule can be introduced into the cell, optionally together with an RNA encoding a desired protein and after predefined time periods the presence of reporter molecule and optionally protein are then determined. Suitable reporter molecules are well known in the state of the art and those commonly used can also be used here. In a preferred embodiment, RFP, red fluorescing protein, is used as the reporter molecule.

As stated above, the RNA according to the invention can be used for therapy so that in the cell into which the RNA is introduced a protein can be formed which is naturally not expressed to the desired extent or at all. Here the RNA according to the invention can be used both when the protein is not formed owing to a deficiency of a gene and also in the cases when owing to a disease a protein is not formed or in cases where the introduction of the protein is advantageous for the body. The RNA can also be used for supplementing a protein which is not expressed to an adequate extent. The dose used in each case depends on the function which the RNA is to fulfill. As stated above, the duration of action of the RNA according to the invention can be deliberately adjusted. The duration of the treatment depends on the particular indication. If the RNA is used for the chronic therapy of a disease due to a deficient gene, the duration of action will be as long as possible, while with other indications it can be deliberately adjusted to a time window.

According to a particularly preferred embodiment, an IVT mRNA which encodes the surfactant protein B is used as the RNA. When this protein is deficient in mammals, it results in the development of the respiratory distress syndrome of the premature and newborn. In the newborn, this syndrome often leads to death owing to a lung disease. The use of a multiply modified in vitro transcribed mRNA encoding SP-B wherein 5 to 50% of the uridine nucleosides and 5 to 50% of the cytidine nucleosides are modified results in the protein being formed and the disease being moderated or cured.

According to a further preferred embodiment, an IVT mRNA which encodes erythropoietin is used as the RNA. Erythropoietin is a very important protein for the body which for example in kidney diseases is no longer available in adequate quantity and therefore must be supplied. Recombinant erythropoietin, which has been produced in microorganisms or animal cells and hence has a glycosylation not occurring naturally, is at present used for this. With the use of the recombinant EPO there were in rare cases severe side effects, for example erythrocyte aplasia.

The IVT mRNA provided according to the invention contains a ribonucleic acid which encodes erythropoietin, wherein 5 to 50% of the uridine nucleotides and 5 to 50% of the cytidine nucleotides are modified. In a particularly preferred embodiment, an EPO-encoding mRNA wherein 15 to 25% of the uridine nucleotides and 15 to 25% of the cytidine nucleotides are modified is provided. It has been found that this mRNA has markedly reduced immunogenicity compared to unmodified RNA. At the same time it displays a transfection efficiency of over 90% and a stability such that the hematocrit value is still elevated after 14 days. Since the EPO produced by the RNA according to the invention in the body has the correct glycosylation, side effects are not to be expected. Through targeted intermittent administration of the EPO-encoding RNA modified according to the invention, the hematocrit value could be kept at the desired level for a prolonged period.

According to the invention, a non-immunogenic stable RNA is provided which is usable in vivo in mammals and provides the necessary protein in a form which is very similar if not identical to the naturally present endogenous protein and in particular has the endogenous glycosylation.

The mRNA according to the invention can be used directly as such. However, there is also the possibility of further modifying the mRNA in order to introduce further beneficial properties. Firstly, the mRNA can be modified by attaching other coding or non-coding sequences to the coding strand. Secondly, it can also be modified by binding further molecules to functional groups provided in the modified nucleotides.

In one embodiment, the mRNA according to the invention can be combined with targeting ligands which bind to surface receptors specific for the target cells, so that a receptor-mediated transfection of the target cell is possible. For this firstly vehicles which are suitable for the introduction of mRNA into cells, or else the mRNA itself can be modified with a ligand. Examples of suitable vehicles for the introduction of mRNA into cells are cationic agents. These include cationic lipids, cationic polymers or also nanoparticles, nanocapsules, magnetic nanoparticles and nanoemulsions. Suitable vehicles are known to those skilled in the art and described in the specialist literature. Suitable ligands are also well known to those skilled in the art and described in the literature and available. As ligands for example transferrin, lactoferrin, clenbuterol, sugar, uronic acids, antibodies, aptamers, etc. can be used.

However, the mRNA itself can also be modified with a ligand. For this, mRNAs with modified nucleosides that bear a primary amino group or an azido group in the 2' position of the ribose are preferred. Examples can be found in the table above. Such modifications are particularly preferred since they contribute to the biological activity. Via these modifications, the ligand can easily be incorporated by amide formation or "click" chemistry, e.g. by bioconjugate techniques.

In a further embodiment, an RNA sequence which can bind to proteins, e.g. receptors, (aptamer) is introduced at the 5' end of the mRNA. This procedure has the advantage that the ligand can already be introduced directly into the matrix at the DNA level and cloned and introduced into the mRNA by the IVT. Hence subsequent modification of the mRNA with the ligand is no longer necessary.

In a further embodiment, the mRNA is modified by additional modification with inert polymers, e.g. polyethylene glycol (PEG). Methods for this are well known to those skilled in the art, and processes such as are known for ligands can be used. Thus for example a binding site for polyethylene glycol, to which the PEG is bound after transcription, can be provided in a small part of the modified nucleotides used for the mRNA according to the invention. The polyethylene glycol serves for the extracellular stabilization of the mRNA, i.e. it protects the polyribonucleotide molecule until it has arrived in the cell. On entry into the cell, the PEG is cleaved off. Hence the bond between PEG and RNA is preferably designed such that the cleavage on entry into the cell is facilitated. For this, for example a functional group can be provided which is pH-dependently cleaved off. Other molecules stabilizing the RNA can also be provided via appropriate active sites on the modified nucleotides. In this way, the mRNA can be protected by steric stabilization against enzymatic degradation and an interaction with components of biofluids prevented. The mRNA thus modified can be designated as "stealth" mRNA.

A preferred method for the protection and stabilization of RNA is described in EP 11 98 489, to the content whereof reference is expressly made here. RNA according to the invention is preferably protected by the methods described in EP 11 98 489. It has been found that firstly the RNA modified according to the invention can also advantageously be stabilized and protected by this method and secondly that the activity of RNA according to the invention thus treated is not or not significantly restricted. Hence in a preferred embodiment of the present invention, RNA modified according to the invention is treated in accordance with EP 11 98 489.

An example of cell-specific regulation is the incorporation of micro-RNA binding sites for micro-RNA 142-3p, which is expressed in hematopoietic cells, but not in cells of other origin. As a result, the expression is controlled such that the mRNA translation in hematopoietic cells is markedly diminished compared to other cells. Similarly, the expression in other cell types can be selectively controlled by incorporation of the relevant suitable micro-RNA binding sites, which are known to those skilled in the art.

In a further embodiment, the mRNA according to the invention is combined with a target or a binding site for at least one micro-RNA which is present only in healthy cells, but not the cells affected by the disease. As a result, the protein encoded by the mRNA is produced only in the cells which need the protein. The selection of the suitable targets is made by routine methods which are well known to those skilled in the art. A common method which is performed at the DNA level is the cloning of a micro-RNA binding site into 3'UTR (Gu et al, Nat Struct Mol Biol. 2009 February; 16(2): 144-50, Brown et al, Nat Biotechnol. 2007 December; 25(12): 1457-67, Brown et al, Nat Med. 2006 May; 12(5): 585-91, WO 2007000668). In a preferred embodiment, an RNA equipped with a binding site for micro-RNA is used when the RNA encodes a cytotoxin. In this case it is especially desirable to bring the protein toxic to cells only where it is intended to deploy its action. For this embodiment, it can also be advantageous to adjust the duration of action of the RNA by specifically modifying the RNA so that its stability lies in a predefined time window.

Further, the RNA according to the invention can be combined with micro-RNAs or shRNAs downstream of the 3' polyA tail. This has the advantage that the mRNA-micro-RNA/shRNA hybrid can be cleaved intracellularly by Dicer and thereby two active molecules which intervene in different pathogenic cascades can be released. Such a hybrid can be provided for the treatment of diseases such as cancer or asthma. Hence the RNA according to the invention is suitable for simultaneously complementing a deficient mRNA and intervening in a defective micro-RNA cascade.

Thus according to the invention, an RNA with advantageous properties is provided which can be tested with a screening method wherein a sequence coding for a reporter protein, e.g. red fluorescing protein (RFP), is used. When the toxicity and stability of sequences of a reporter gene with unmodified, singly or multiply modified nucleotides with different modifications are tested for their immunogenicity and transfection efficiency, it is found that only the mRNA according to the invention, i.e. modified multiply, wherein at least 5% respectively of the uridine nucleosides and cytidine nucleosides are replaced by modified nucleosides leads to a markedly reduced immunogenicity towards human primary monocytes in the blood and at the same time can yield high transfection rates of more than 80%. This can for example be tested in alveolar epithelial cells type II in humans or in the mouse. Moreover, the duration of the RNA expression for RNAs modified according to the invention is significantly longer than with known RNA. It has been found that mainly owing to the higher stability and lower immunogenicity of the mRNA multiply modified according to the invention the expression lasts longer than with known preparations. In a quantitative assessment, a derivative modified according to the invention showed a 10 times higher quantity of expression product 10 days after the transfection than non- or only singly modified RNA.

A further subject of the invention is a method for the screening of nucleotide sequences in order to test the immunogenicity and expression quality, wherein the mRNA sequence is contacted with at least one receptor selected from TLR3, TLR3, TLR8 and helicase RIG-1 and the binding capacity measured in comparison with a control sequence. As the control sequence, a sequence is used the binding capacity whereof is known. The weaker the binding to at least one of these receptors is, the more promising is the sequence.

The properties of mRNA according to the invention, in particular IVT mRNA, can be tested with a screening method on an RNA expressing a reporter protein. The red fluorescing protein (RFP) is preferred as the reporter protein. Sequences encoding this protein which have nucleotides with different modifications can be tested for their immunogenicity and transfection efficiency. Thus various modifications of mRNA can be used for tests, e.g. uridine nucleosides can be partially replaced by 2-thiouridine nucleosides (also referred to below as s2U) and cytidine nucleosides can be partially replaced by 5-methylcytidine nucleosides (also referred to below as m5C).

FIGS. 1A, 1B, 1C, 2A and 2B show the results which are obtained on performing such a screening method. More detailed particulars are to be found in the examples. The results shown in the figures are based on experiments which were performed for RFP RNA and show that only multiply modified mRNA wherein at least 5% of the uridine nucleosides and at least 5% of the cytidine nucleosides respectively are modified lead to markedly reduced immunogenicity towards human primary monocytes in the blood, both ex vivo and in vivo, and at the same time can yield high transfection rates of more than 80% both in alveolar epithelial cells type II in humans and also in the mouse. Moreover, the duration of the expression for mRNAs modified according to the invention is significantly longer than for unmodified mRNA.

In a further embodiment, a method is provided for testing whether an RNA under consideration is suitable for therapy, with the use of an mRNA immunoprecipitation test (RIP). A suitable RIP test is described in more detail in the examples. Studies have shown that cells of the immune system are activated by unmodified reporter mRNA via RNA binding to Toll-like receptor (TLR) 3, TLR7, TLR8 and helicase RIG-1. When the results show that the binding of a tested mRNA to TLR3, TLR7, TLR8 and/or RIG-1 is markedly decreased compared to unmodified mRNA this is an indication of decreased immunogenicity. It could be shown that in this respect multiple modifications used according to the invention are significantly more effective than single s2U modifications. In the examples, the influence of RNA on the level of IFN-γ, IL-12 and IFN-α was studied, after the RNA had been injected intravenously into mice. It was found that multiply modified $s2U_{(0.25)}m5C_{(0.25)}$ RFP mRNA prevented an immune response. The results obtained in the examples together show that multiply modified mRNA significantly decreases the TLR and RIG-1 binding and hence lowers the immune response with at the same time elevated and prolonged expression. Hence a multiply modified RNA, in particular IVT mRNA, is a suitable candidate for the in vivo treatment of a disease due to a deficient gene. A particularly promising candidate is briefly explained below and described in more detail in the examples.

In order to test whether it is possible to use RNA modified according to the invention for treatment in the lung, multiply modified mRNA which codes for a fusion protein of enhanced green fluorescent protein and luciferase (EGFP-Luc) was introduced directly into the lung of a mouse and tested as to whether luciferase was expressed in comparison with unmodified EGFPLuc RNA. The luciferase expression reached a maximum after three hours in the lung, although the total luminescent flux rapidly declined after 24 hours to very low proportions 5 days after the treatment. In contrast to this, high expression values were observed up to 5 days after the treatment in mice which had been treated with multiply modified EGFPLuc mRNA.

In a particularly preferred embodiment, an RNA is provided whose therapeutic potential allows treatment of the disease attributable to SP-B deficiency, namely $s2U_{(0.25)}$ m5C$_{(0.25)}$ SP-B mRNA. SP-B is a relatively small amphipathic peptide which is encoded by a single gene and through proteolytic processing creates a precursor with 381 amino acids in type II alveolar epithelial cells which coat the alveoli. It improves the distribution, adsorption and stability of the surfactant lipids which are necessary for the reduction of the surface tension in the alveoli. With a deficiency of SP-B, symptoms such as thickened alveolar walls, cellular infiltration and interstitial edema occur. This lung damage is accompanied by congestion, i.e. an increased number of erythrocytes and an increased number of macrophages, neutrophils and corresponding proportions of inflammatory cytokines in the broncho-alveolar fluid. The congenital deficiency in humans and studies on transgenic mice have proved that SP-B plays an essential role in survival after birth. Congenital SP-B deficiency, which arises through mutations in the SP-B gene, is critical for the replacement of the surfactant and leads to a fatal failure of the respiratory tract in the newborn during the first months of life. Hence a lung transplant is the only currently available therapeutic intervention. Hence an mRNA therapy for SP-B deficiency, which is rendered possible with the RNA according to the invention, is an important alternative treatment.

The RNA according to the invention can be used for the treatment of this disease, preferably with perfluorocarbon as vehicle. Hence in a preferred embodiment a pharmaceutical preparation comprising perfluorocarbon and s2U$_{(0.25)}$m5C$_{(0.25)}$ SP-B mRNA is provided. This combination makes it possible to reconstitute SP-B in the lung of patients with SP-B deficiency, so that the chances of survival are increased. Because of the high stability of the RNA according to the invention, administration at regular intervals, e.g. 1 to 3 times weekly is sufficient for this. Preferably the SP-B mRNA is administered for this intratracheally as an aerosol by spraying at high pressure. It has been found that the mRNA according to the invention can ameliorate the symptoms described above and thus improve the lung function, which can be demonstrated by testing of the lung parameters, as described in detail in the examples.

The mRNA according to the invention can be effectively used in therapeutic procedures and makes a treatment of diseases due to missing or defective proteins possible. Systemic administration of the multiply modified mRNA is possible. There can be cases wherein the mRNA translation in cells which are not affected by the gene defect is undesirable, e.g. because undesired side effects arise. In order to have the mRNA translated selectively only in the cells which need the encoded protein, e.g. in cells in which a gene defect exists, the corresponding vector can either be supplemented by sequences which enable addressing of the tissue affected, e.g. via ligands. In a further embodiment, sequences to which endogenous micro-RNAs bind, which are not expressed in the target cell, can be added to the vector which contains the mRNA, so that the mRNA are degraded in all cells which contain the relevant endogenous micro-RNAs, while they are retained in the target cells. Thus side effects can be minimized.

The RNA according to the invention can be administered in a manner known per se to patients who need the protein or protein fragment encoded by RNA, e.g. because they have a disease due to a deficient gene. For this, the RNA is formulated as a pharmaceutical preparation with normal pharmaceutically acceptable additives. The form of the preparation depends on the location and the nature of administration. Since the RNA according to the invention is characterized by particularly high stability, it can be formulated in many ways, depending on where and in what form it is to be used. It has been found that the RNA according to the invention is so stable that it can be freeze-dried, processed in this form, e.g. crushed or milled, and stored, and can then be reconstituted when required and retains its biological activity.

When the RNA is administered systemically, it is usually formulated as an injectable liquid with normal additives such as agents adjusting the tonicity and stabilizers, preferably as a unit dosage form. As stabilizers, those normally known, such as for example lipids, polymers and nanosystems or liposomes, are used. In a preferred embodiment, a composition suitable for parenteral administration is provided which contains RNA modified according to the invention which encodes EPO.

In a preferred embodiment, particularly when the RNA encodes SP-B protein, the RNA according to the invention is provided in a form suitable for uptake via the lung, e.g. by inhalation. Suitable formulae for this are known to those skilled in the art. In this case the preparation is in a form which can be introduced into the respiratory tract via normal nebulizers or inhalers, e.g. as a liquid for nebulizing or as a powder. Devices for administration as liquid are known, and ultrasound nebulizers or nebulizers with a perforated oscillating membrane which operate with low shear forces compared to nozzle jet nebulizers are suitable. Also suitable are powder aerosols. Both mRNA complexed with cationic lipids and also bare mRNA is available after the freeze-drying with the sugar sucrose as powder that can then be crushed to a respirable size and moreover shows biological activity.

In a preferred embodiment, a pharmaceutical composition intended for pulmonary administration is combined with perfluorocarbon, which is administered previously or simultaneously with the pharmaceutical composition in order to increase the transfection efficiency.

In a further preferred embodiment, RNA modified according to the invention is provided in a delayed release polymer as a carrier for the coating of implants. For this the RNA modified according to the invention can be used as such or else an RNA protected with a coating polymer and/or polymer complex.

A further subject of the invention are implants on the surface whereof there is a coating of a delayed release polymer which contains RNA which encodes beneficial factors for the ingrowth of the implant. According to the invention both coatings which contain mRNA which encodes only one factor and also coatings which contain mRNAs which encode several factors, e.g. various growth factors or growth factors and angiogenesis factors or further factors promoting ingrowth, are possible here. The various factors can also be provided in a form such that they are released at staggered intervals.

Furthermore, the expression "RNA which encodes one or more growth factors and one or more angiogenesis factors" should be understood to mean both an RNA sequence which encodes more than one protein, singly or as a fusion protein, and also a mixture of different RNA sequences which encode different proteins, where each RNA sequence encodes one protein.

The invention is further explained by the following examples.

EXAMPLE 1

Figure 1A:
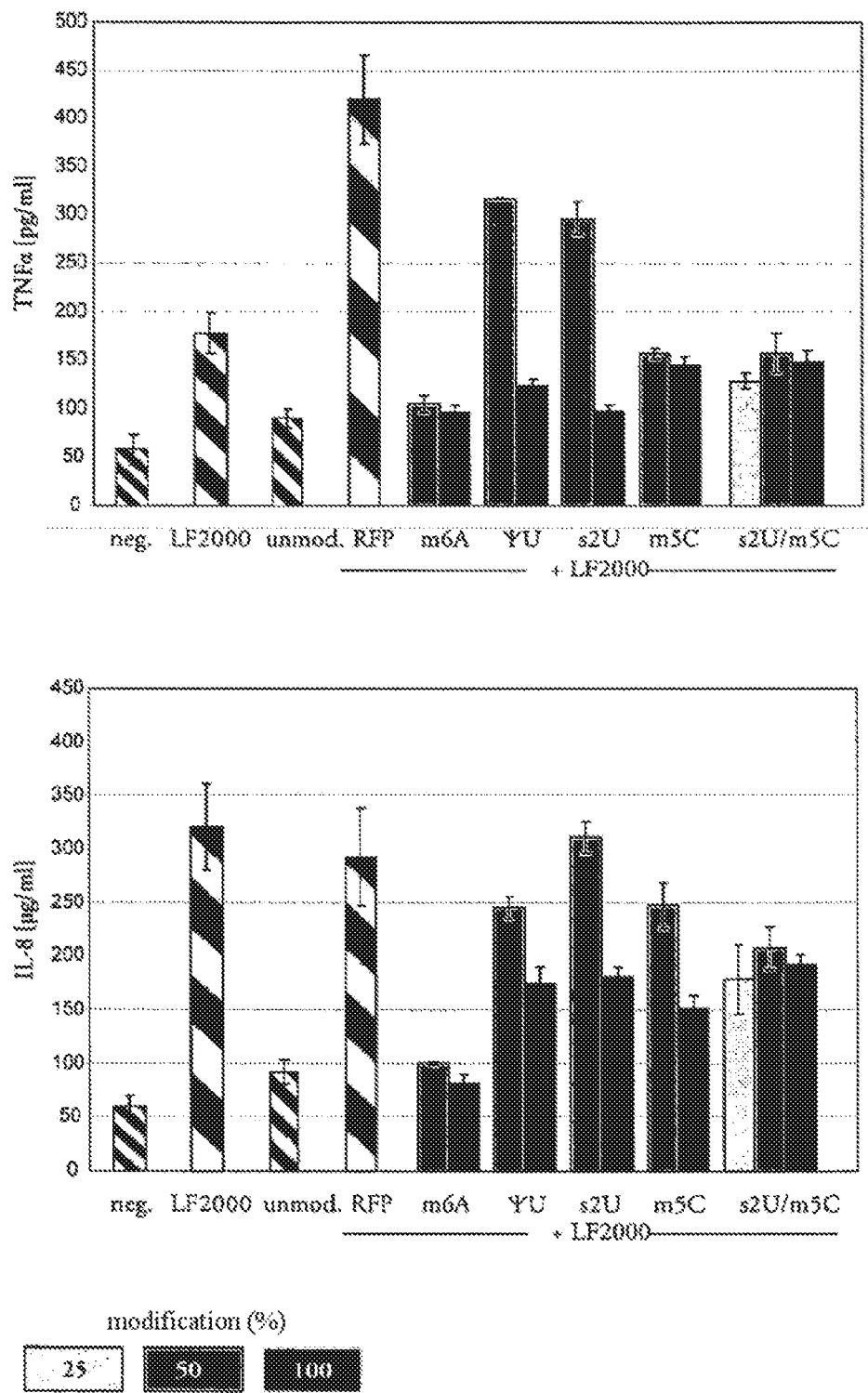
Figure 1B:
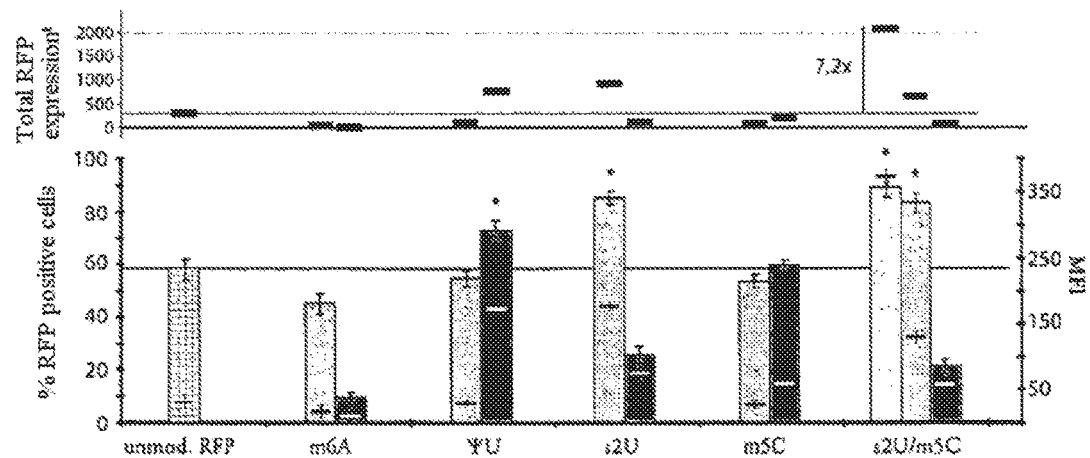
Figure 1C:
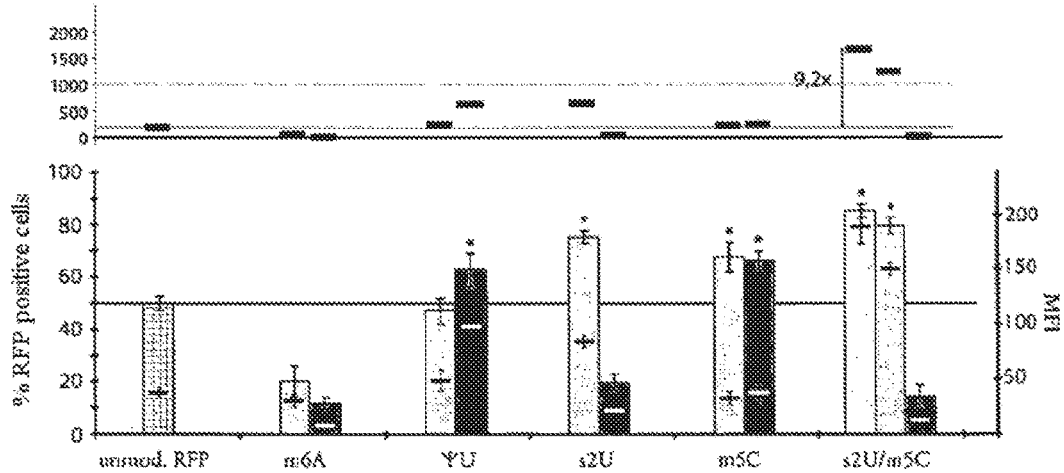
Figure 1C:
Figure 2A:
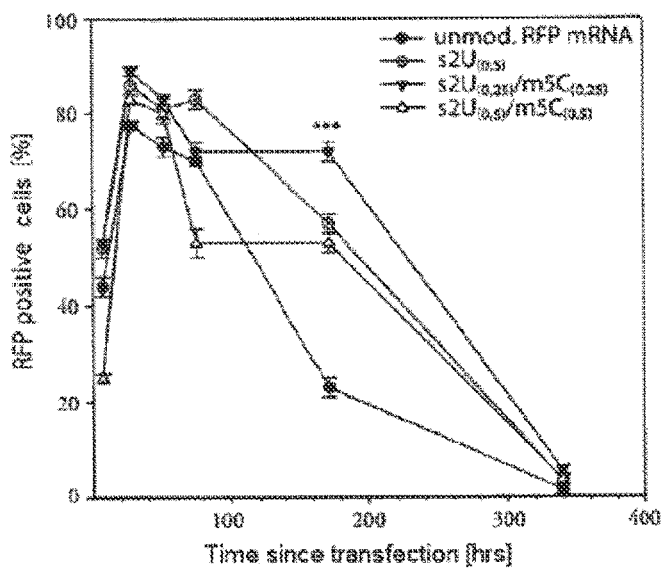
Figure 2B:
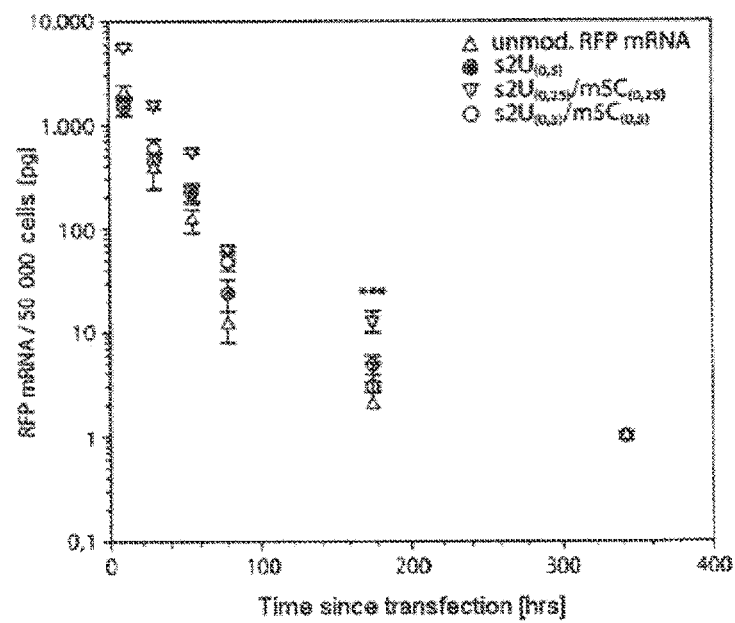
Figure 4:
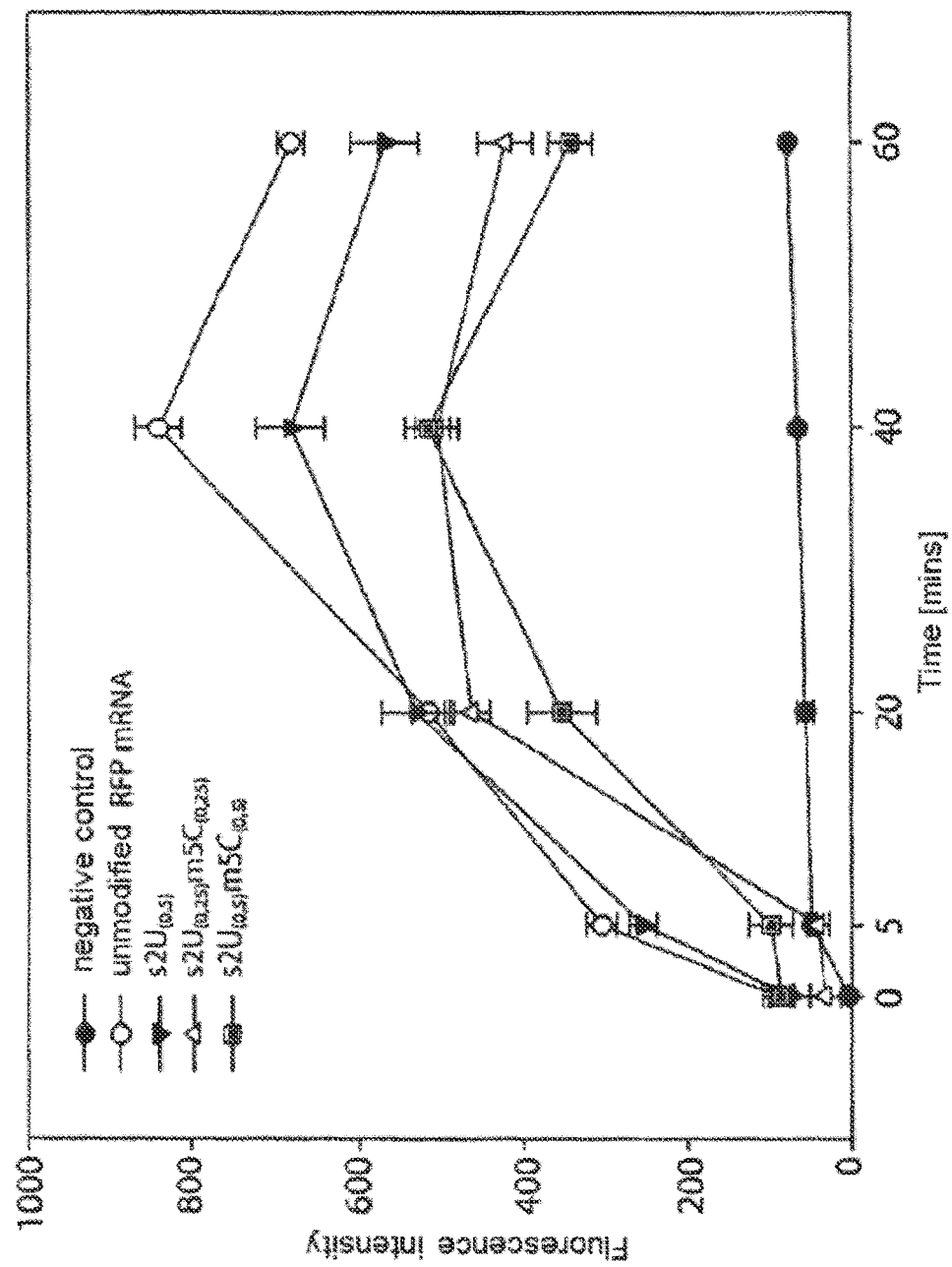
FIG. 4 shows a diagram in which the fluorescence intensity of the RFP produced was plotted against time for unmodified and differently modified mRNAs. The modified mRNA is translated later and less strongly compared to the unmodified mRNA.
Figure 5:
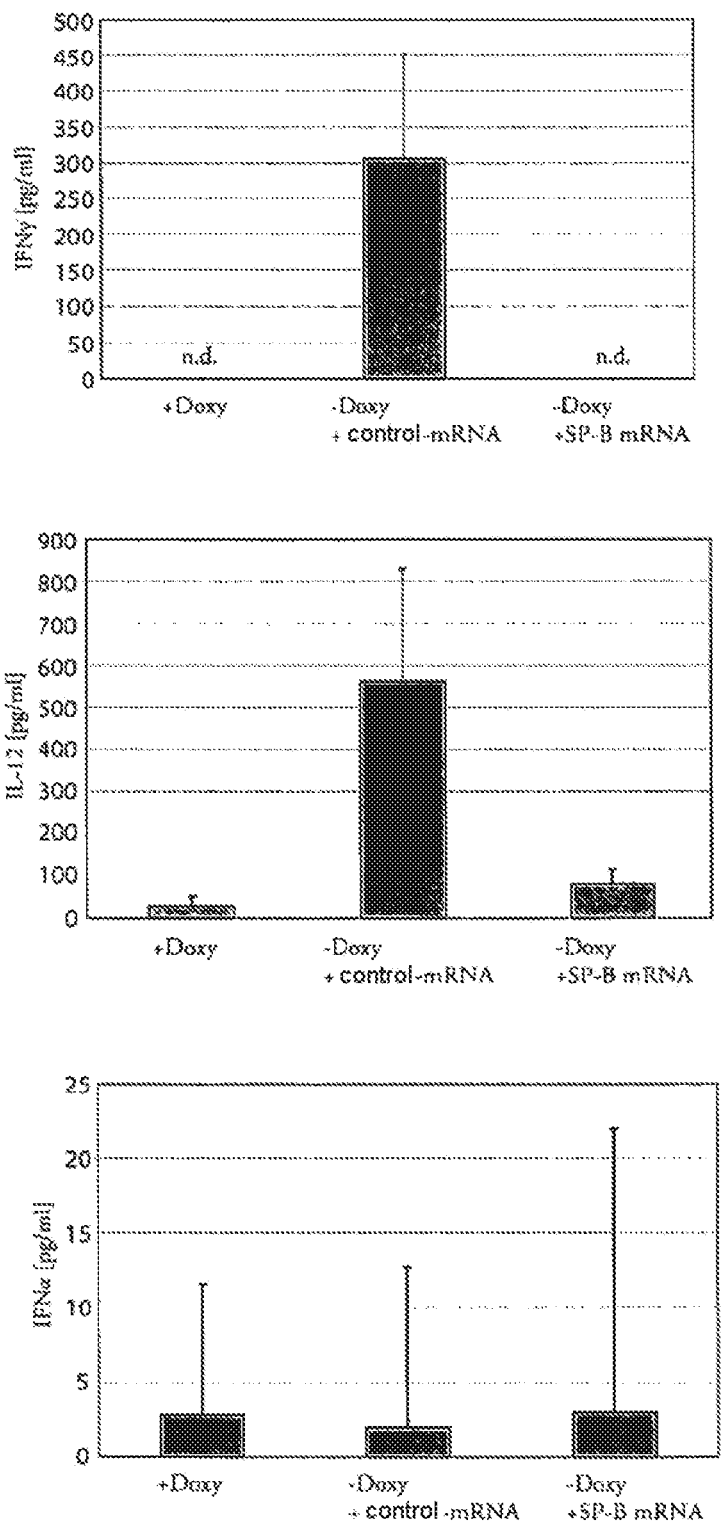
FIG. 5 shows three diagrams in which inflammatory markers for mice treated with different mRNAs are plotted. It can clearly be discerned that RNA modified according to the invention causes no inflammatory reactions, while unmodified RNA leads to a strong immune reaction.

In order to be able to assess the therapeutic utility of an IVT mRNA, it was assessed whether non-immunogenic IVT mRNA could be obtained for in vivo use. Hence in a first step, in vitro transcribed mRNA for red fluorescing protein (RFP) with modified nucleosides was investigated with regard to immunogenicity and transfection efficiency. The results show that multiply modified mRNA wherein 25% of the uridine is replaced by 2-thiouridine (s2U) and 25% of the cytidine by 5-methylcytidine (m5C) yields $s2U_{(0.25)}m5C_{(0.25)}$ IVT mRNA which has markedly reduced immunogenicity towards human primary mononuclear blood cells, as shown in FIG. 1A, and a high transfection rate of more than 80% in epithelial cells of the alveolar type II both in humans (FIG. 1B) and also in the mouse (FIG. 1C). Moreover, the duration of the mRNA expression was significantly prolonged (FIG. 2A). The results show that this prolonged expression is mainly due to the higher stability of the mRNA multiply modified according to the invention. An absolute quantitative assessment showed an approximately 10 times greater quantity of $s2U_{(0.25)}m5C_{(0.25)}$ RFP mRNA 7 days after the transfection (FIG. 2B). The translation efficiency was somewhat diminished for the modified RFP mRNA and hence could not contribute to higher and longer activity (FIG. 4).

Figure 2C:
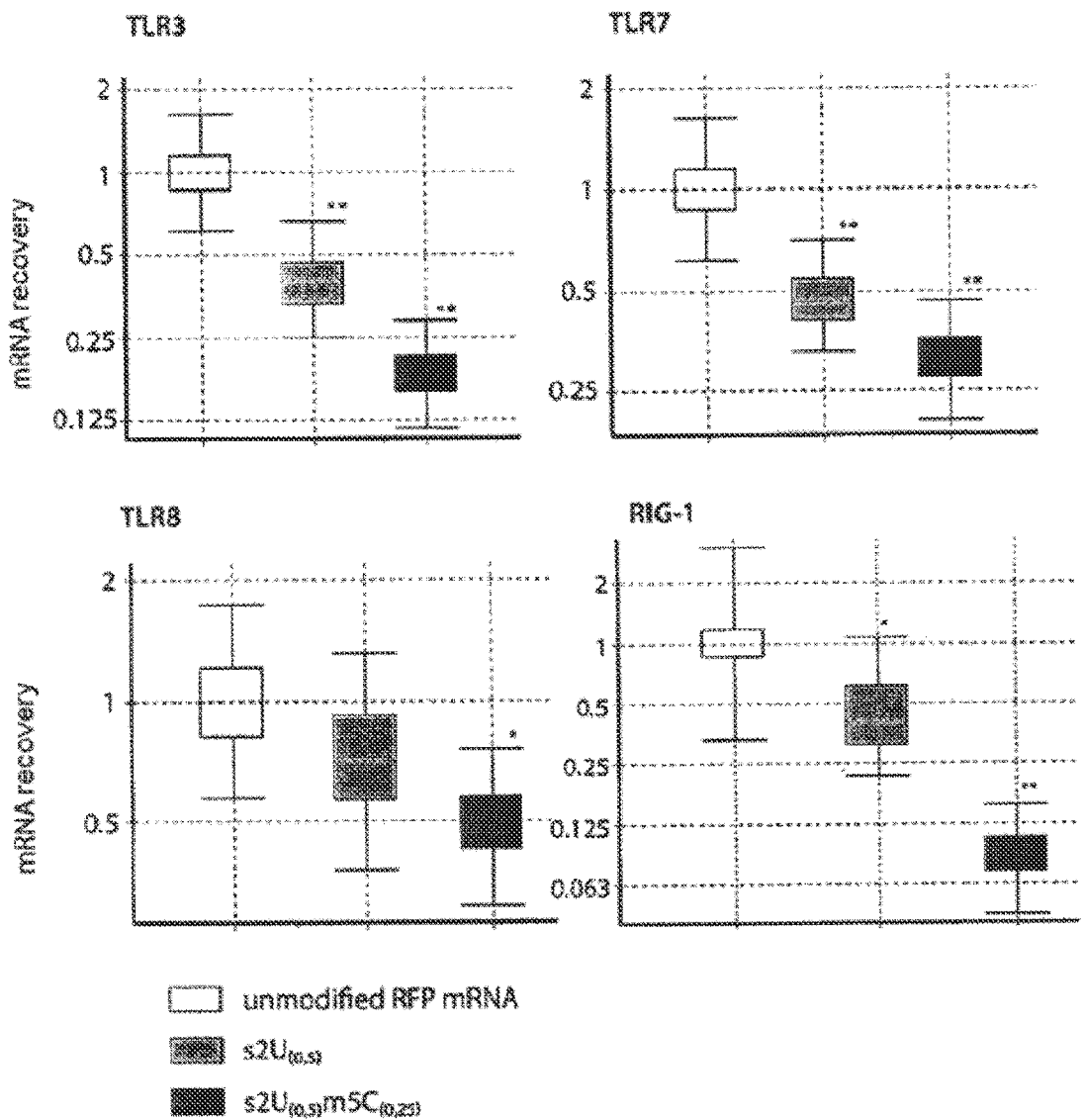
Figure 2D:
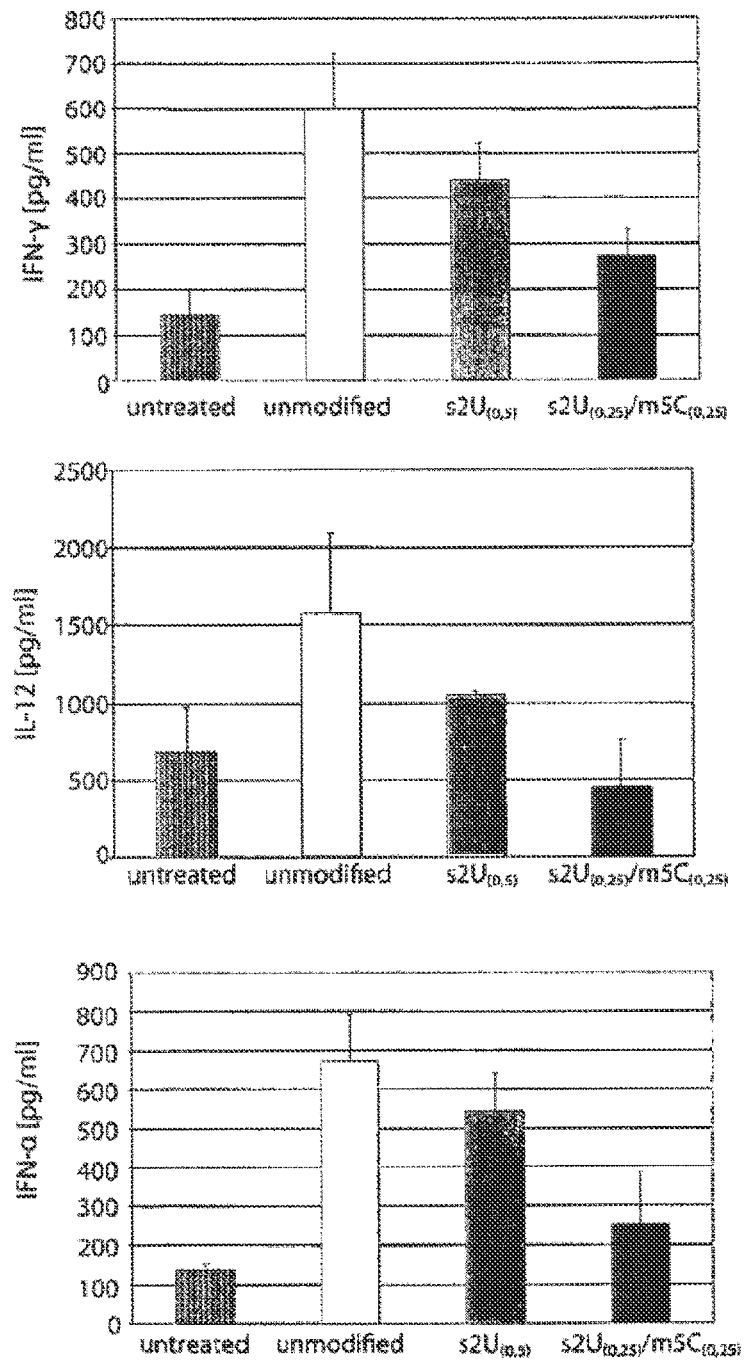

In the next step, the mechanism on which the reduced immune response is based was investigated using a modified RNA immunoprecipitation test (RIP assay). Studies have shown that cells of the immune system are activated by unmodified reporter mRNA (1) by RNA binding to Toll-like receptor (TLR) 3 (2), TLR7 (3), TLR8 (4) and helicase RIG-1 (5). The results show that the binding of the multiply modified RFP mRNA according to the invention to TLR3, TLR7, TLR8 and RIG-1 was markedly reduced compared to unmodified RFP mRNA. In this respect, the multiple modifications were considerably more effective than a single s2U modification (FIG. 2C). As was to be expected from the binding studies, unmodified RFP mRNA increased IFN-γ, IL-12 and IFN-α to a considerable extent when it was injected intravenously into mice, while multiply modified $s2U_{(0.25)}m5C_{(0.25)}$ RFP mRNA prevented an immune response (FIG. 2D). Overall, these results show that the mRNA multiply modified according to the invention markedly decreased the TLR and RIG-1 binding and thereby the immune response, and at the same time increased and prolonged expression, which makes such mRNA a very promising candidate for in vivo tests.

Figure 3A:
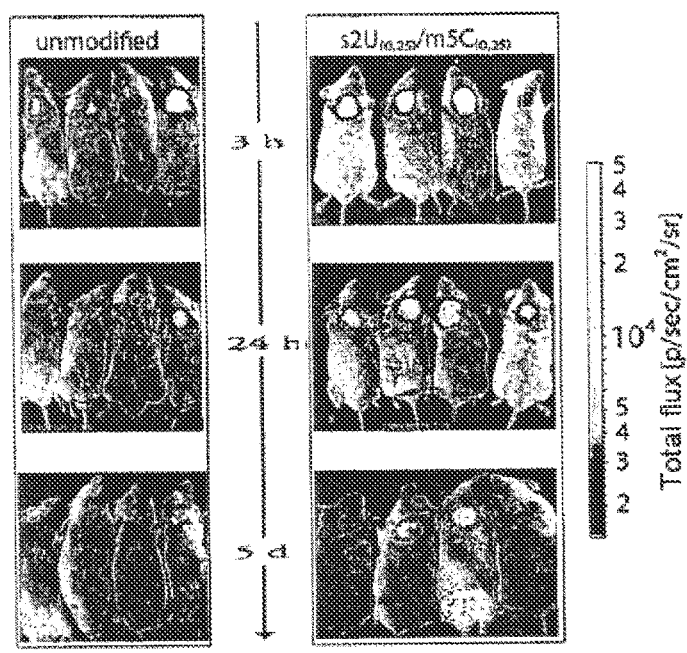
Figure 3B:
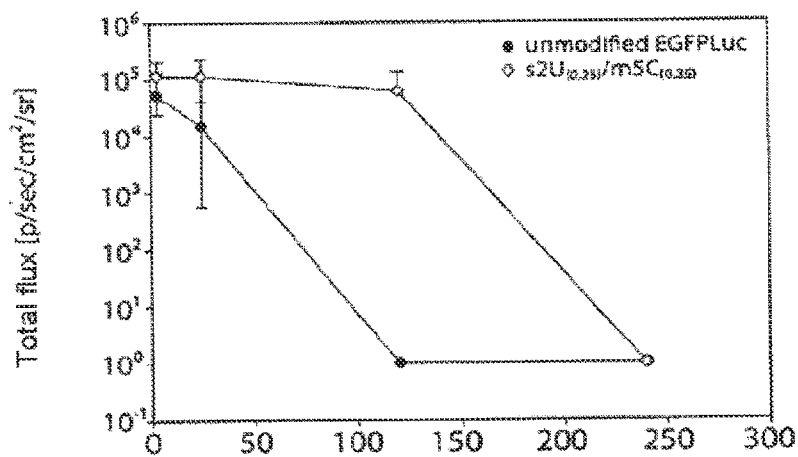

It was therefore tested whether an $s2U_{(0.25)}m5C_{(0.25)}$ mRNA which encoded a fusion protein of enhanced green fluorescent protein and luciferase (EGFPLuc) which was introduced directly into the lungs of the mouse could intensify and prolong the luciferase expression in vivo in comparison to unmodified EGFPLuc mRNA. For this purpose, a high pressure spray device for intratracheal administration known per se as described for example in (6) was used, perfluorocarbon (fluorinated FC-77) being administered beforehand in order to increase the transfection efficiency (7). After 3 hours the luciferase expression reached a maximum in the lungs in vivo, although the total luminescence rapidly decreased after 24 hours to a low level 5 days after the treatment (FIGS. 3A and B). In contrast to this, high expression values were observed up to the $5^{th}$ day after the treatment in mice which were treated with $s2U_{(0.25)}m5C_{(0.25)}$ EGFPLuc mRNA (FIGS. 3A and B).

This shows that the therapeutic potential of the multiply modified mRNA according to the invention for therapy is very promising. Hence an $s2U_{(0.25)}m5C_{(0.25)}$ SP-B mRNA multiply modified according to the invention was tested for the treatment of SP-B deficient mice. SP-B is a relatively small amphipathic peptide which is encoded by a single gene and in epithelial cells of the alveolar type II is converted by proteolytic processing into a precursor with 381 amino acids which coats the alveoli (8, 9). It improves the distribution, adsorption and stability of the surface-active lipids which are necessary for the reduction of the surface tension in the alveolus. If the gene for this protein is deficient, disorders in the respiratory tract occur after birth which can rapidly lead to death. It has been observed that a hereditary defect in humans and in transgenic mice plays an important part in postmortal survival (10). A hereditary SP-B deficiency which arises through mutations in the SP-B gene prevents the formation of the surface-active lipids, which leads to respiratory failure during the first months after birth (11). A lung transplant is the only therapeutic intervention that is currently possible (12). Hence an mRNA therapy for SP-B deficiency would be an alternative treatment to ensure viability with this deficiency.

Figure 3C:
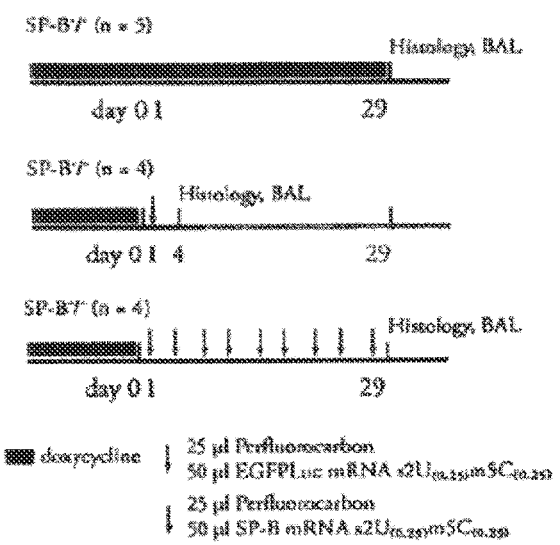
Figure 3D:
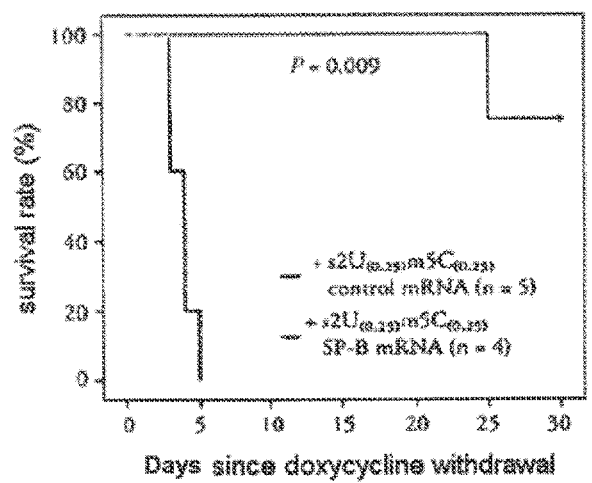
Figure 3E:
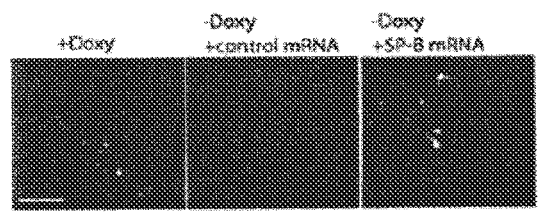
Figure 3G:
Figure 3H:
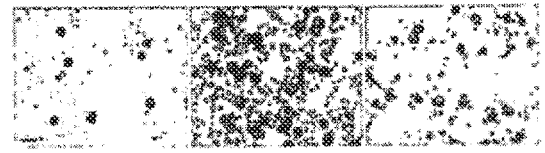
Figure 3F:
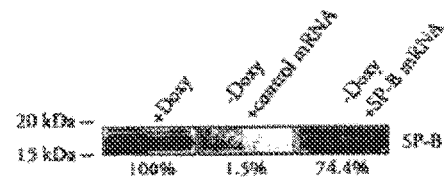
Figure 3I:
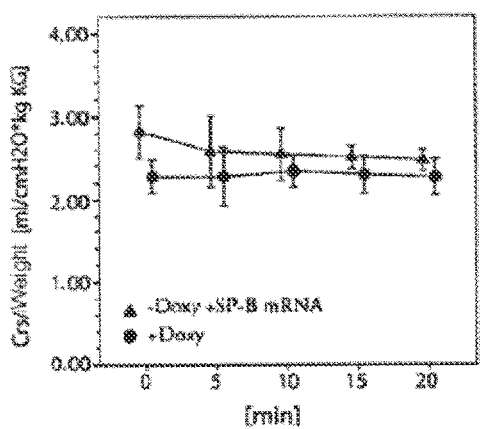

Hence a knockout mouse model for SP-B deficiency was selected in order to test a gene therapy with multiply modified mRNA of SP-B according to the invention. For this a mouse model was chosen wherein the mouse SP-B cDNA was expressed under the control of exogenous doxycycline in SP-B$^{-/-}$ knockout mice. Withdrawal of doxycycline in adult SP-B$^{-/-}$ mice resulted in a decreased content of SP-B in the lung, which resulted in respiratory failure when the SP-B concentration fell below 25% of the normal level. Conditioned transgenic mice which received doxycycline survived normally (13, 14). The therapeutic strategy used comprised the following: (i) pre-treatment of the mice with perfluorocarbon before the introduction of SP-B mRNA, in order to increase expression and (ii) repeated use of SP-B mRNA twice weekly every third or fourth day for four weeks (FIG. 3C). In order to perform an experiment to demonstrate this principle, $s2U_{(0.25)}m5C_{(0.25)}$ SP-B mRNA was administered intratracheally as an aerosol into conditional SP-B$^{-/-}$ mice using a high pressure nebulizer. This treatment saved the mice from respiratory failure and extended their average lifespan to 28.8±1.1 days (FIG. 3D), up to the defined endpoint of the study. In contrast to this, after withdrawal of the doxycycline, untreated SP-B$^{-/-}$ mice displayed symptoms of an acute respiratory problem within 3 to 4 days. This was also observed after administration of perfluorocarbon alone or perfluorocarbon with $s2U_{(0.25)}m5C_{(0.25)}$ EGFPLuc mRNA as a control, the mice then dying within 3.8±0.4 days (FIG. 3D, and data not shown). Moreover, successful reconstitution of SP-B in the lungs of the mice treated with $s2U_{(0.25)}m5C_{(0.25)}$ SP-B mRNA was confirmed by immunostaining (FIG. 3E) and semiquantitative Western blot analysis (FIG. 3F) for SP-B. The pulmonary histology was normal in mice which had been treated for 4 weeks with $s2U_{(0.25)}m5C_{(0.25)}$ SP-B mRNA, while the lungs of the mice which had received $s2U_{(0.25)}m5C_{(0.25)}$ EGFPLuc control mRNA displayed thickened alveolar walls, cellular infiltration and interstitial edema after 4 days (FIG. 3G). This lung damage was accompanied by congestion (elevated number of erythrocytes) and an elevated number of macrophages and neutrophils and an elevated level of inflammatory cytokines (FIG. 3H) in the broncho-alveolar lavage fluid (BALF), while this was largely prevented in the mice treated with SP-B mRNA. It has been shown that the withdrawal of doxycycline worsened pulmonary function without treatment (14, 15). It has been observed that prolonged treatment of SP-B$^{-/-}$ mice with $s2U_{(0.25)}m5C_{(0.25)}$ SP-B mRNA maintained the normal pulmonary function, as in the SP-B$^{-/-}$ mice which received doxycycline (FIG. 3I).

To summarize, these results show that all functional and pathological parameters of the SP-B deficiency in the lung improved substantially and were comparable with conditional SP-B$^{-/-}$ mice which received doxycycline.

The results show the therapeutic efficacy of the multiply modified mRNA in a mouse model for a lethal lung disease. However, the further application of the mRNA therapy can still be improved as follows: (i) undesired mRNA translation in cells of unaffected tissue could lead to undesired effects outside the target region, (ii) if the multiply modified mRNA also reaches unaffected tissue, an adequate quantity of mRNA must be provided and (iii) repeated dosing is necessary for short-duration mRNA activity. In order to improve this, micro-RNA biology can be enlisted in order to prevent undesired mRNA translation in cells not affected by the disease. By incorporating target sequences of endogenous micro-RNAs, which are not expressed in the target cell, mRNA degradation can be selectively caused in cells not affected by the disease, during which however the mRNA is retained in the target cells, as a result of which side effects are minimized (16, 17).

In a further approach, release systems, the targeting ligands, which bind specific receptors to cell surfaces, can be combined, so that receptor-mediated transfection of the target cell is enabled. Since mRNA can be produced in large quantities nowadays (18) and efficient production processes for the production even of multiply modified mRNA on a large scale are possible, the clinical use of the mRNA according to the invention is possible and this makes it possible to develop mRNA systems specifically tailor-made for each disease (19, 20), whereby the dosing frequency and the short-duration activity can be kept to a minimum, which is not possible with the currently known therapies. In this way, according to the invention an effective molecular therapy for the treatment of disease due to a gene deficiency is provided.

EXAMPLE 2

In order to show that in SP-B deficient mice an improvement in condition or an increase in life expectancy is achieved merely by the use of the mRNA modified according to the invention which encodes SP-B, a further experiment was performed. The mouse model and conditions as described in example 1 were used.

Three groups of mice were set up. One group of SP-B deficient mice received mRNA modified according to the invention twice in one week (B), a second group received mRNA modified according to the invention twice a week for 28 days (C), and for comparison a third group of mice received modified EGFP-Luc mRNA (A).

It was found that the mice which received no SPB mRNA modified according to the invention died after a short time. The mice which received the RNA according to the invention survived only as long as they were given the SP-B RNA according to the invention. This proves that the RNA according to the invention is biologically active and can replace necessary protein.

In detail, the experiment was performed as follows. SP-B KO mice, as described in example 1, received either modified EGFP-Luc mRNA (A) (n=10) or modified SP-B mRNA twice in one week (B) (n=4) or modified SP-B mRNA twice a week for 28 days (C) (n=4). Kaplan-Meier survival curves were plotted and a Wilcoxon-Gehan test performed. It was found that the intratracheal administration of the doubly modified SP-B mRNA twice within one week into the lungs of transgenic SP-B mice (B) in which the SP-B gene is controlled by the addition of doxycycline in the drinking water prolongs the average survival time of the mice after withdrawal of the doxycycline from the drinking water before the start of the treatment to 10.2±0.5 days (B) in comparison to 3.4±0.2 days after administration of an EGFP-Luc control mRNA.

The results are presented in the diagram of FIG. 12. It is found that the intratracheal administration of the doubly modified SP-B mRNA according to the invention is in fact life-saving. Without addition of the mRNA according to the invention, the mice die after a short time. This experiment also shows firstly that SP-B mRNA produces the SP-B necessary to life in vivo and secondly that the SP-B mRNA must be administered continuously to protect the experimental animals from death.

EXAMPLE 3

In a further experiment in which the mice described in example 1, which all received doxycycline, were used, it was investigated whether the RNA according to the invention causes inflammatory reactions in an early phase after administration. For this, 5 groups were set up and cytokine levels, IFNγ and IL-12 were measured in the bronchoalveolar lavage of mice 8 hours after administration of different preparations. The six groups received the following preparations: a) control, untreated, i.e. neither perfluorocarbon nor RNA, b) control, perfluorocarbon, c) control, perfluorocarbon and unmodified SP-B mRNA, d) invention, perfluorocarbon and modified s2U$_{(0.25)}$m5C$_{(0.25)}$ SP-B mRNA and e) control, perfluorocarbon and SP-B plasmid DNA, (n=4). In each case 20 µg (50 µl) of a preparation were administered. The results are shown in FIG. 13. In FIG. 13, the mean value±standard error is shown. The following abbreviations were used in FIG. 13: Doxy—doxycycline, Pfc—perfluorocarbon, pDNA—plasmid DNA (*P<0.05 compared with the untreated group).

The results show that on intratracheal administration of unmodified mRNA or plasmid DNA the inflammatory marker IL-12 is markedly elevated in the bronchoalveolar lavage, while the administration of doubly modified mRNA leads to no rise in IL-12 in comparison to untreated mice. The administration of doubly modified mRNA does slightly increase the level of the inflammatory marker IFNγ, but only as far as is also observed after administration of perfluorocarbon. In contrast to this, the administration of unmodified mRNA or the administration of plasmid DNA also leads to a marked rise in the IFNγ level. Thus using the mRNA modified according to the invention an inflammatory reaction is not to be expected, while the administration of unmodified mRNA or even plasmid DNA very rapidly causes inflammatory reactions.

EXAMPLE 4

In order to demonstrate the possibilities for use of the mRNA modified according to the invention, various types of modifications and their effect on the transfection and translation efficiency and on immunogenicity were studied. A459 cells were transfected with 200 ng of mRNA in each case and how many of the cells had been transfected and in how many cells the fluorescent protein had been translated was then investigated. This evaluation was made using the mean fluorescence intensity (MFI). The results are shown in FIG. 10A. mRNA modified according to the invention was tested and in comparison to this an mRNA modified not according to the invention, in which two different modifications of uridine nucleotides were used and non-modified mRNA. The mRNA molecules modified according to the invention were:

s2U/m5C and s4U/m5C wherein the modified nucleotides each had a content of 10% and RNA molecules which in addition to 10%/10% s2U/m5C and s2U/5mC each contained a further 5% of modified nucleotides, namely once $C_2'NH_2$ and once 5% $G'N_3$. The results show that the mRNA modified according to the invention displays a very high transfection efficiency, while unmodified mRNA and mRNA modified not according to the invention each show far lower transfection and translation efficiency.

The immunogenicity was also tested for the modified mRNA previously described, by investigating the TNF-α level on human PBMCs after administration of 5 μg of each mRNA. The results are shown in FIG. 10B. As is clearly seen, the TNF-α level is markedly elevated on administration of unmodified mRNA or with mRNA wherein two types of modified uridine nucleotides were used. The TNF-α level is lower by at least 50% with the RNAs modified according to the invention than with unmodified RNA.

EXAMPLE 5

Method for the production of multiply modified mRNA according to the invention.

a) Constructs for the In Vitro Transcription

For the in vitro transcription of RFP cDNA (678 bp), a plasmid, pCS2+DsRedT4, containing an SP6 promoter was used. For the in vitro transcription of SP-B cDNA (1146 bp), a pVAX1 plasmid (Invitrogen) containing a T7 promoter was used. In order to create the vector for the in vitro transcription of EGFPLuc (2.4 kb), a pST1-2β-globin-UTR-A-(120) construct containing a T7 promoter which was obtained as described in (19) was used. The constructs were cloned using standard techniques of molecular biology.

Production of Modified mRNA

In order to create templates for the in vitro transcription, the pCS2+DsRed.T4, EGFPLuc and SP-B plasmids were linearized with XbaI. The linearized vector DNAs were purified with the NucleoSpin Extract II kit (Macherey-Nagel) and assessed by spectrophotometry. The in vitro transcription was performed with the mMESSAGE-mMACHINE SP6 or T7 Ultrakit (Ambion). The SP-6 kit capped the mRNA with 7-methylGpppG, while the T7 kit created the analogous antireverse cap (ARCA; 7-methyl-(3'-O-methyl)GpppGm$^7$G(5')ppp(5')G in a transcription reaction with ultrahigh yield. In order to produce RNA modifications, the following modified ribonucleic acid triphosphates were added to the reaction system in the stated ratios: 2'-thiouridine 5'-triphosphate, 5'-methylcytidine 5'-triphosphate, pseudouridine 5'-triphosphate and $N^6$-methyladenosine 5'-triphosphate (all from TriLink BioTechnologies and checked for purity with HPLC and $^{31}$P NMR). After the in vitro transcription, the RNA from the pVAX1 SP-B plasmid was enzymatically polyadenylated using the poly(A) tail kit (Ambion). The poly(A) tails were approximately 200 nt long. All capped mRNAs (RFP, EGFPLuc and SP-B) were purified using the MEGAclear kit (Ambion) and analyzed for size and purity with the Agilent RNA 6000 Nano Assay on a Bioanalysis Instrument 2100 (Agilent Technologies).

Cell Transfections

Lung Cell Transfection

Type II alveolar epithelial cell lines from humans and from the mouse, A549 and MLE12 respectively, were grown in Minimal Essential Medium (Invitrogen) which was supplemented with 10% fetal calf serum (FCS), 1% penicillin-streptomycin and 0.5% gentamycin. One day before the transfection, 80 000 cells per well were plated out in 24-well plates. The cells (more than 90% confluence) were transfected with 200 ng of mRNA with the use of Lipofectamin 2000 (Invitrogen) according to the manufacturer's instructions. After 4 hours, the cells were washed with PBS and serum-containing medium was added. For analyses of long-term expression, the cells were regularly subdivided (when the confluence was >90%).

Human PBMC Transfection

Human PBMCs (CTL-Europe GmbH) cryoconserved in liquid nitrogen were carefully thawed at 37° C. using CTL Anti-Aggregate Wash Supplement, during which sterile-filtered RPMI-1640 (Invitrogen) was slowly added. For all experiments described, a single characterized batch of PBMCs was used in order to make the data reproducible.

Flow Cytometry

A flow cytometry analysis was performed on the A549 and MLE12 cells which had been transfected with RFP mRNA, as described above. The cells were removed from the plate surface with 0.25% trypsin/EDTA, washed three times with PBS and again suspended in PBS in order to measure the fluorescence using an FACSCalibur (BD Biosciences). The transfection efficiency was calculated from the percentage of the cell population which exceeded the fluorescence intensity of the control cells, which had only been treated with PBS. At least 2500 cells per tube were counted. The data were analyzed with Cellquest Pro.

Cytokine Detection

Enzyme-linked immunosorbent assays (ELISA) were performed using human IL-8 and TNF-α kits (RayBio), mouse IFN-γ and IL-12 (P40/P70) kits (RayBio) and mouse IFN-α kit (RnD Systems).

Real Time In Vitro Translation 500 ng of RFP mRNA was in vitro translated using Retic Lysate IVT (Ambion). Methionine was added to a final concentration of 50 μM. The mixture was incubated at 30° C. in a water-bath, samples were withdrawn at various times and the fluorescence intensity at 590 nm measured on a Wallac Victor$^2$ 1420 Multilabel Counter (Perkin Elmer).

Quantitative RT-PCR

The total RNA was extracted from A549 cells with RNeasy Minikit (Qiagen) or from human PBMCs (see RIP protocol below) and subjected to a reverse transcription (RT) in a batch of 20 μl using the iScript cDNA synthesis kit (Bio-Rad) in accordance with the product manual. cDNA was amplified using the iQ SYBR Green Supermix and iCycler (Bio-Rad) in double batches with the following primers: RFP: 5'-GCACCCAGACCGCCAAGC (forwards) and RFP: 5'-ATCTCGCCCTTCAGCACGC (backwards). C$_t$ values were obtained using the iCycler IQ software 3.1 (Bio-Rad) which automatically calculated the baseline cycles and threshold values.

RNA Immunoprecipitation (RIP)

1×10$^6$ human PBMCs (CTL-Europe GmbH) were transfected with 5 μg of mRNA using 12.8 μl of Lipofectamin 2000 in 1 ml of OptiMEM 1. After 4 hours, the media were supplemented with 10% FCS. After 24 hours, the cell suspension was transferred into tubes and the cells were pelletized by 10 minute centrifugation at 350 rpm. Next a modified version of the ChIP-IT Express protocol (Active-Motive) was used in order to perform the RIP. DEPC-treated water (Serva Electrophoresis) was used for the preparation of all necessary reagents. In accordance with the ChIP-IT manual, the fixing solution and then the glycine stop-fix solution and ice-cold 1×PBS were added to the cells and the cells were pelletized at 4° C. Then the cells were again suspended in lysis buffer to which the protease inhibitors PIC and PMSF had been added, and incubated for 30 mins on ice. After 10 minute centrifugation at 2400 rpm at 4° C., the supernatant was subjected to the capture reaction. The TLR-mRNA/RIG-mRNA complexes were captured overnight on magnetic beads in 8-well PCR strips, as described in the ChIP-IT Express manual. In addition, SUPERase RNase inhibitor (Applied Biosystems/Ambion) was added to a final concentration of 1 U/μl. Anti-human TLR3 mouse IgG1, TLR7 rabbit IgG1, TLR8 mouse IgG1 (all from Imgenex) and RIG-1 rabbit IgG1 (ProSci Incorporated) were used as antibodies. After the washing of the magnetic beads, the TLR-mRNA/RIG-mRNA antibody complexes were eluted, reverse crosslinked and treated with proteinase K in accordance with the ChIP-IT Express protocol. Finally, the eluted mRNA was subjected to a reverse transcription and a quantitative RT-PCR, as described above.

In Vivo Bioluminescence

D-luciferin substrate was dissolved in water, the pH adjusted to 7 and the final volume adjusted such that a concentration of 30 mg/ml was reached. 50 μl of this solution were applied onto the nostrils of the anesthetized mice and absorbed by snuffling (1.5 mg luciferin/mouse). After 10 mins, the bioluminescence was measured with an IVIS100 imaging system (Xenogen) as described in (21) using the following camera settings: visual field 10, fl f-stop, high resolution and illumination times from 1 to 10 mins. The signal in the pulmonary region was quantitatively assessed and analyzed, the background being subtracted using the Living Image Software Version 2.50 (Xenogen).

Animal Studies 6 to 8 week old female BALB/C mice (Charles River Laboratories) were kept under specific pathogen-free conditions and kept in individually ventilated cages with a 12-hour light: 12-hour dark cycle and supplied with food and water ad libitum. The animals were acclimatized for at least 7 days before the start of the experiments. All animal manipulations were approved and were checked by the local ethical committee and performed according to the guidelines of the German Animal Protection Law. For all experiments except for the injection into the caudal vein, the animals were anesthetized i.p. with a mixture of medetomidine (0.5 mg/kg), midazolam (5 mg/kg) and fentanyl (50 μg/kg). After each experiment, an antidote which consisted of atipamezol (50 μg/kg), flumazenil (10 μg/kg) and naloxone (24 μg/kg) was administered to the animals s.c. Blood for the ELISA tests was obtained at various times by puncture of the retrobulbar vein using heparinized 1.3 mm capillaries (Marienfeld).

Injection into the Caudal Vein

25 μg of RFP mRNA were mixed in vivo with Megafectin (MP Biomedicals Europe) in a ratio of mRNA to lipid of 0.25 and Enhancer-3 was added in accordance with the manufacturer's recommendation. The integrity and particle size of the injected complexes was determined with dynamic light scattering (DLS) using a Zeta-PALS/zeta potential analyzer (Brookhaven Instruments Corp.). The mice were laid in a restrainer and 100 μl of the mRNA/Megafectin solution (equivalent to 5 μg of mRNA) were injected into the caudal vein within 30 seconds using a 27 gauge needle and a 1 ml syringe.

Intratracheal Administration by High Pressure Nebulization

BALB/c and SP-B$^{-/-}$ mice were anesthetized as described in (14) and immobilized on a plate system (Halowell EMC) such that the upper teeth were at an angle of 45°. A modified cold light otoscope Beta 200 (Heine Optotechnik) was used in order to optimally illuminate the pharynx. The lower jaw of the mouse was opened with a small spatula and blunt forceps were used to push the tongue aside and maximally expose the oropharynx. A model 1A-1C microsprayer which was connected to a model FMJ-250 high pressure syringe (both from PennCentury Inc.) was inserted endotracheally and 25 μl of Fluorinert FC-77 (Sigma) and 25 μl of luciferase mRNA solution (10 g) or 50 μl of SP-B mRNA solution (20 g) were successively applied. After 5 secs the microsprayer syringe was withdrawn and the mouse was taken from the support after 5 mins.

Pulmonary Function Measurements

Homozygotic SP-B$^{-/-}$ mice±doxycycline±modified mRNA were anesthetized as described above. To prevent spontaneous breathing, vecuronium bromide (0.1 mg/kg) was injected intraperitoneally. The pulmonary mechanical measurements were performed as described in (22). In brief, a blunt steel cannula (external diameter 1 mm) was inserted in the trachea with tracheostomy. The piston pump respirator served both as respirator and also as a measurement device (flexiVent, SAV). During the tidal ventilation, the respirator was set to controlled volume- and pressure-restricted ventilation (Vt=10 μl/g, Pmax=30 cm $H_2O$, PEEP 2-3 cm $H_2O$ at 2.5 Hz and 100% oxygen). The Vt used was 8.4±1.4 μl/g in animals which were receiving doxycycline and 8.9±0.4 μl/g BW in animals which were receiving doxycycline and mRNA (N.S.). The dynamic-mechanical properties of the respiratory system and also the pulmonary entry impedance were measured at 5 minute intervals in animals after insufflation twice at 15 μl/g for 1 sec in order to create a standard volume history. For the oscillatory measurement, the ventilation was stopped at the PEEP level. In order to determine the impedance of the respiratory system ($Z_{rs}$) by forced oscillations (FOT), which consisted of a pseudorandom oscillatory signal of 8 secs, an amplitude of 3 ml/g was used. The forced signal had frequencies between 1.75 and 19.6 Hz (23, 24). The data were collected at 256 Hz and analyzed with a window of 4 secs with 66% overlap. The pulmonary impedance data were represented as resistance (real part) and reactivity (imaginary part) of the respiratory system within the frequency domain. The pulmonary impedance data (Zrs) were subdivided using the constant phase model of the lung, as proposed by Hantos et al. (25). In this model, Zrs consists of a respiratory resistance (Rn), a respiratory tract inertia (inertia), a tissue elasticity ($H_L$) and a tissue damping ($G_L$) according to the equation:

$$Zrs=Raw+j\omega law+(G_L-jH_L)/\omega^\alpha,$$

wherein ω is the angular frequency and ω the frequency dependence of Zrs ($\omega=(2/\omega \tan^{-1}(1/\omega))$). The pulmonary hysteresivity (eta=$G_L/H_L$) is a measure of the lung tissue composition, wherein both the tissue damping and also the tissue elasticity are included (26, 27). For each measurement the constant phase model is automatically tested for fit. The fit quality is represented as the coherence of the determination (COD), and the data are rejected if the COD is below 0.85.

Analysis of the Surfactant Protein

The total protein content of the lavage supernatants was determined with the Bio-Rad protein assay kit (Bio-Rad). 10 μg of total protein were separated under non-reducing conditions on NuPage 10% bis-tris gels using a NOVEX Xcell II mini-cell system (Novex). After the electrophoresis, the proteins were transferred onto a PVDF membrane (ImmobilonP) with a NuPage blot module (Novex). Surfactant protein B (SP-B) was detected with polyclonal rabbit antiserum which was directed against SP-B (c329, gift from Dr W. Steinhilber, Altana AG) and an improved chemiluminescence test (Amersham Biosciences) was then performed with horseradish peroxidase conjugated polyclonal goat anti-rabbit anti-IgG (1:10 000, Dianova). Under these conditions, the test could detect about 2.5 ng of SP-B per track (28). As the chemiluminescence detection system, DIANA III dev. 1.0.54 with the Aida image analyzer (Ray test Isotopenmessgerate GmbH) was used and the data were quantitatively assessed with Quantity One 4.6.7 (Bio-Rad).

Fluorescence Microscope Analysis

Sections fixed (3% paraformaldehyde) and embedded in paraffin wax were subjected to immunohistochemistry as recommended by the manufacturer (Abcam, www.abcam.com/technica). The slides were incubated with anti-human anti-mouse SP-B antibody and with Texas red-conjugated anti-rabbit IgG antibody (both from Abcam, 1:500) and counterstained with DAPI. Fluorescent images were obtained by Zeiss Axiovert 135.

Statistics

Differences in mRNA expression between groups were analyzed by pairwise fixed reallocation randomization tests with REST 2005 software (29). The half-lives for the decay of the bioluminescence were calculated with Prism 5.0. All other analyses were performed using the Wilcoxon-Mann-Whitney test with SPSS 15 (SPSS Inc.). The data are stated as mean value±SEM (standard error of the mean value) or as median±IQR (interquartile ranges) and $P<0.05$ (two-sided) was regarded as statistically significant.

EXAMPLE 6 mRNA Multiply Modified According to the Invention which Encodes EPO

With a method essentially as described in example 3, modified mRNA was produced which contained an EPO-encoding part. The expression efficiency of this mRNA was tested. For this, 5 g of mRNA modified according to the invention or of non-modified mRNA were injected i.m. into mice. Each group of mice had four members. On day 14 and day 28 after administration of the RNA, the content of EPO in the serum was assessed quantitatively with an ELISA test. The hematocrit value was assessed in whole blood from mice in the same experiment. The data shown in the appended FIG. 11 each represent the mean value±SEM. The scatter blot shows the individual hematocrit values. Bars show median values. $*P<0.05$ compared to the untreated group at each time point; $+P<0.05$ compared to the unmodified mEPO group at each time point.

(c) The data show the mean value±SEM. Human PBMCs were transfected with 5 µg of unmodified or modified RFP mRNA and the recovery rates were determined with RIP using antibodies specific for TLR-3, TLR-7 and TLR-8. The boxes signify mean values±IQR. The lines show the minimum and maximum values. $*P<0.5$, $P<0.01$, $*P<0.001$ compared to unmodified mEPO group.

(d) 5 µg of unmodified and modified mEPO mRNA were injected intravenously into mice (n=4 for each). After 24 hours, the interferon-γ, IL-12 and interferon-α levels in the serum were assessed quantitatively by ELISA.

As can be seen from the diagrams, for the RNA modified according to the invention the inflammatory markers are in the non-pathological range, while for unmodified RNA or modified RNA only with modified uridine nucleotides the inflammatory markers are markedly elevated.

Thus according to the invention an mRNA which encodes EPO is provided which is very stable and at the same time causes few or no immunological reactions. Such an mRNA can advantageously be used for the treatment of erythropoietin deficiency. Because of the high stability, administration is only necessary every 2 to 4 weeks.

EXAMPLE 7

It was investigated how the repeated administration of EPO-encoding mRNA modified according to the invention affects the hematocrit values. This was to show whether the mRNA modified according to the invention also remains active over a longer period when it is administered into the body. An immunological reaction to the mRNA according to the invention would for example decrease the activity.

Hence 10 µg of modified mEPO mRNA (as described in example 6) were administered to mice intramuscularly on days 0, 21 and 34 (n=10). The hematocrit value was then determined in the whole blood from the mice on days 0, 21, 34, 42 and 51. The results are shown in FIG. 14. The data in the diagram show the mean±standard error. $*P<0.05$ compared to the hematocrit value on day 0.

The results confirm that repeated administration of the mRNA modified according to the invention leads to a long-lasting elevation of the hematocrit value. This shows that the mRNA remains active, even when it is administered many times.

EXAMPLE 8 mRNA modified according to the invention is also suitable for bringing proteins promoting healing or ingrowth into the vicinity of implants in order thus to promote the healing process or the ingrowth. In order to show that the mRNA modified according to the invention is stably and lastingly expressed when it is applied in the form of a coating on titanium surfaces, a coating which contained mRNA which encoded luciferase was applied onto titanium plates. It was then investigated whether and for how long luciferase could be detected in the vicinity, free or in cells.

Two sequences encoding different proteins were used for the experiment, namely an RNA for luciferase which is secreted from the cell expressing it, as a model for proteins which are to be released into the vicinity, such as for example growth factors or angiogenesis factors. Further, RNA which encodes a luciferase which is not secreted but remains in the cell was used as a model for proteins which are to have some kind of effect in the cell. For the secretion model, RNA which encoded Metridia luciferase was used, wherein compared to the wild type 25% of the uridine units were replaced by s2U and 25% of the cytidine units were replaced by m5C. For the non-secretion protein model, a firefly luciferase-encoding mRNA was used wherein likewise 25% of the uridine units were replaced by s2U and 25% of the cytidine units were replaced by the modified m5C.

It was found that the mRNA preparations according to the invention, which were protected as a complex with polymer, after release from the coating material remained active and were expressed over a prolonged period. It was found that the respective protein encoded by the mRNA modified according to the invention could be detected over a prolonged period.

For the tests, the mRNA modified according to the invention, protected by a polymer complex, was embedded in a carrier material which was applied as a layer onto titanium plates. The carrier material was polylactide (PDLLA), a well-known material for this purpose, which can selectively release the contained mRNA gradually. An advantage of such a coating is that the release can be specifically adjusted. The results show that the polylactide fragments released on degradation do not impair the activity of the mRNA, so that this system is very suitable. The mRNA itself is stabilized by a coating polymer.

For the experiments, Metridia luciferase-encoding plasmid DNA (pDNA) or modified mRNA was used. 9 μg respectively of Metridia luciferase pDNA or doubly modified $s2U_{(0.25)}m5C_{(0.25)}$ mRNA in 200 μl of $H_2O$ (+ if necessary 500 μg of lactose) were complexed with 9.4 μg of L-PEI (L-polyethyleneimine) in 200 μl of $H_2O$. After this, the complexes were introduced into 100 μl of a coating polymer solution (2.4 μl of 409.1 mM P6YE5C) and lyophilized overnight (the coating polymer P6YE5C was prepared as described in EP 11 98 489). After this, the complexes were suspended in 72 μl of a PDLLA (poly-DL lactide)/EtOAc (50 mg/ml PDLLA) mixture on ice and dispersed by means of a micropotter. Autoclaved titanium plates (r=3 mm, 18 μl each) in a 96-well plate were coated with this dispersion. After a further lyophilization overnight, A549 cells in 200 μl of RPMI-1640 medium were added (5000 cells/200 μl). From the second day, 50 μl of the supernatant were taken in each case, the medium changed and the Metridia luciferase expression determined on the following days by means of 100 μl of coelenterazine solution (0.003 mM final concentration) for each.

In a further experiment, the activity of the Metridia luciferase-encoding mRNA modified according to the invention was tested when this had been deposited onto calcium phosphate particles and introduced into the coating in this form. For this, 4 μg of Metridia luciferase $s2U_{(0.25)}m5C_{(0.25)}$ mRNA in 600 μl of 1×HBS were mixed each time with 33 μl of 2.5M $CaCl_2$. After 30 mins, autoclaved titanium plates (r=3 mm, 18 μl each) in a 96-well plate were coated with this. After lyophilization overnight, A549 cells in 200 μl of RPMI-1640 medium were added (5000 cells/200 μl). From the second day, 50 μl of each supernatant were taken, the medium changed and the Metridia luciferase expression determined on the following days by means of 100 μl of coelenterazine solution (0.003 mM final concentration) for each.

The results can be seen in the diagram in FIG. 15. The results show clearly that mRNA modified according to the invention stays active even when it is protected with a polymer coating, introduced into a delayed release matrix and applied onto titanium implants. Moreover the mRNA modified according to the invention remains biologically active and is continuously translated into the encoded protein. The secretion capacity is also retained, which is seen from the fact that the Meridia luciferase can be detected in the cell culture medium (as a model for secreted bone growth factors such as for example BMP-2). In addition, the results surprisingly show that the coating with modified mRNA yields higher protein expression than the coating of titanium implants with the analogous plasmid DNA. When the mRNA/PEI complexes are provided with a coating polymer before the incorporation into the titanium implant coating, still higher protein expression is obtained than with the use of the same complexes, but without coating polymer (in the figure mod. mRNA/lPEI-P6YE5C). Moreover it was found that the addition of lactose as an additive is possible without the modified mRNA losing its biological activity.

The results also show that modified mRNA precipitated onto calcium phosphate particles retains its activity and can exercise its advantageous properties in the titanium implant coating. The biological activity is retained. This is of particular importance since calcium phosphate can be directly incorporated into the bone.

As indicated above, a further experiment was performed with firefly luciferase-encoding DNA or RNA. For this, 9 μg of firefly luciferase pDNA or modified $s2U_{(0.25)}m5C_{(0.25)}$ mRNA respectively in 200 μl of $H_2O$ were complexed with 9.4 μg of L-PEI in 200 μl of $H_2O$. After this, the complexes were introduced into 100 μl of a coating polymer solution (2.4 μl of 409.1 mM P6YE5C) and lyophilized overnight. Next, the complexes were dissolved in 72 μl of a poly-DL-lactic acid (PDLLA)/ethyl acetate (EtOAc) (50 mg/ml PDLLA) mixture on ice and dispersed by means of a micropotter. Autoclaved titanium plates (r=3 mm, 18 μl each) in a 96-well plate were coated with this dispersion. After a further lyophilization overnight, A549 cells in 200 μl of RPMI-1640 medium were added (5000 cells/200 μl). On the second day, 1 μl of 350 μM D-luciferin were added to each well, incubated for 20 mins and the luciferase expression determined by bio-imaging. The results are shown in FIG. 16. As can be seen from the diagram on FIG. 16, titanium implants can be coated with mRNA modified according to the invention during which the mRNA also further remains biologically active and translates the encoded protein. The protein formed remains in the cell and can be detected intracellularly. In addition, the results show that the coating with modified mRNA leads to higher protein expression than the coating of titanium implants with the analogous plasmid DNA.

EXAMPLE 9

In order to control the expression of the mRNA modified according to the invention so that the encoded protein is only expressed in cells in which it is wanted, but not in other cells, a micro-RNA binding site was incorporated into the mRNA in order to enable cell-specific regulation of the mRNA expression.

For this, HEK293 cells were cultured in MEM with 10% FCS and 1% penicillin-streptomycin. 24 hrs before the transfection, 100 000 cells/well were sown into a 24-well plate. Directly before the transfection, the medium was replaced by 400 μl of Optimem (Invitrogen). U937 cells were cultured in RPMI-1640 medium with 10% FCS and 1% penicillin-streptomycin. Directly before the transfection 800 000 U937 cells in 400 μl of Optimem medium (Invitrogen) per well were sown into a 24-well plate. For each well, 100 ng of EGFP mRNA and 250 ng of RFP miRNA-BS mRNA (see below) were diluted to 50 μl with Optimem. 2 μl of Lipofectamine 2000 were made up to 50 μl with Optimem and incubated for 5 mins at room temperature. Next the mRNA solution was pipetted into the Lipofectamine 2000 solution and incubated for a further 20 mins at room temperature. The resulting solution was pipetted into the wells with the cells and after 4 hrs penicillin-streptomycin (5 μl) was added and the incubation continued overnight in the incubator. After this, the HEK293 cells were washed with PBS and detached from the floor of the wells by addition of trypsin before being centrifuged for 5 mins at 300 G. The U937 cells were also centrifuged for 5 mins at 300 G. The supernatant was removed and the respective cells then washed twice with PBS. Next the cells were resuspended in 500 μl of PBS for the FACS analysis. In FIGS. 17A and 17B, the ratio of the expression of EGFP to the expression of RFP is shown as the number of positive cells (FIG. 17A) and as the mean RFP fluorescence intensity (FIG. 17B).

The results show that by the incorporation of a micro-RNA binding site into in vitro transcribed mRNA the expression can be cell-specifically regulated. In the RFP miRNA-BS mRNA, the untranslated sequence of a fourfold repetition of a micro-RNA binding site, which are separated from one another by short spacing sequences, is situated 3' from the RFP sequence and 5' from the polyA tail (SEQ ID No.1). A micro-RNA binding site which binds to the micro-RNA 142-3p was used. This micro-RNA is expressed in hematopoietic cells such as U937 cells, but not in cells of other origin, such as HEK-293 cells. When micro-RNA 142-3p binds to the RFP miRNA-BS mRNA, e.g. in the U937 cells, the degradation of the mRNA is initiated by RNA interference. As a result the formation of RFP is decreased, i.e. fewer cells express RFP at lower intensity than in cells in which micro-RNA 142-3p is not present. In order to show that this principle also functions well with the mRNA modified according to the invention, U937 and HEK-293 cells were each co-transfected with EGFP mRNA (without micro-RNA binding site) and RFP miRNA-BS mRNA (with fourfold tandem repetition of the micro-RNA binding site for the micro-RNA 142-3p) and the expression of EGFP and RFP then measured by FACS. Since the RFP miRNA-BS mRNA is degraded because of RNA interference more rapidly in U937 cells than in HEK-293 cells, while the EGFP mRNA is equally stable in both cells, it is expected that the ratio of EGFP to RFP will be higher in HEK-293 cells than in U937 cells. This could be confirmed in the experiments performed. The diagram shows clearly that the number of RFP-positive U937 cells after normalization to the number of EGFP-positive cells is markedly lower than in HEK-293 cells. The same applies for the quantity of RFP formed per cell. The results thus also show clearly that the scale of the biological activity of in vitro transcribed mRNA can be controlled after transfection in cells by the incorporation of micro-RNA binding sites. The mRNA translation can thus be suppressed in cells in which the mRNA translation is undesired. Side effects can also be reduced thereby.

The mRNA used for the experiments in this example has the following sequence (SEQ ID No.1). The RFP sequence is shown with a gray background. The underlined sequence shows the fourfold tandem repetition of the micro-RNA binding site for the micro-RNA 142-3p with spacing sequences (see FIG. 18). After synthesis, the sequence was cloned into the vector pVAX1 using BamHI-EcoRv.

REFERENCES

1. K. Kariko et al., *Mol Ther* (Sep. 16, 2008)
2. L. Alexopoulou. A. C. Holt, R. Medzhitov, R. A. Flavell, *Nature* 413, 732 (Okt 18, 2001)
3. S. S. Diebold, T. Kaisho, H. Hemmi, S. Akira, C. Reis a Sousa, *Science* 303, 1529 (Mar. 5, 2004)
4. F. Hell et al., *Science* 303, 1526 (Mar. 5, 2004)
5. M. Yoneyama et al., *Nat Immunol* 65, 730 (July, 2004)
6. M. Bivas-Benita, R. Zwier, H. E. Junginger, G. Borchard, *Eur J Pharm Biopharm* 61, 214 (Okt, 2005)
7. D. J. Weiss et al., *Mol Ther* 8, 927 (Dez, 2003)
8. T. E. Weaver. J. A. Whitsett, *Am J Physiol* 257, L100 (Au, 1989)
9. S. W. Glasser et al., *Proc Natl Acad Sci USA* 84, 4007 (June 1987)
10. J. A. Whitsett, T. E. Weaver, *N Engl J Mod* 347, 2141 (Dez 26, 2002)
11. L. M. Nogee, D. E. de Mello, L. P. Dehner, H. R. Colten, *N Engl J Med* 328, 406 (Feb. 11, 1993)
12. A. Hamvas et al., *J Pediatr* 130, 231 (February, 1997)
13. J. C. Clark et al., *Proc Natl Acad Sci USA* 92, 7794 (Aug. 15, 1995)
14. K. R. Melton et al., *Am J Physiol Lung Cell Mol Physiol* 288, L543 (September 2003)
15. M. Ikegami, J. A. Whitsett, P. C. Martis, T. E. Weaver, *Am J Physiol Lung Cell Mol Physiol* 289, L962 (Dez, 2005)
16. B. D. Brown, M. A. Venneri, A. Zingale, L. Sergi Sergi, L. Naldini, *Nat Med* 12, 585 (Mai, 2006)
17. B. D. Brown et al., *Nat Biotechnol* 26, 1457 (Dez, 2007)
18. S. A. McKenna et al., *Nat Protoc* 2, 3270 (2007)
19. S. Holtkamp at al., *Blood* 108, 4009 (Dez 15, 2006)
20. M. L. Read et al., *Nucleic Acids Res* 33, e88 (2005)
21. M. K. Aneja, R. Imker, C. Rudolph, *J Gene Med* 9, 967 (November 2007)
22. P. Dames et al., *Nat Nanotechnol* 2, 495 (August 2007)
23. J. J. Pillow, T. R. Korfhagen, M. Ikegami, P. D. Sly, *J Appl Physiol* 91, 2730 (Dez 2001)
24. T. F. Schuessler, J. H. Bates, *IEEE Trans Biomed Eng* 42, 860 (September 1995)
25. Z. Hantos, A. Adamicza, E. Govaerts, B. Daroczy, *J Appl Physiol* 73, 427 (August 1992)
26. C. M. Alleyne, I. D. Frantz, 3rd, J. J. Fredberg, *J Appl Physiol* 66, 542 (February 1989)
27. P. D. Sly, R. A. Collins, C. Thamrin, D. J. Turner, Z. Hantos, *J Appl Physiol* 94, 1460 (April 2003)
28. M. Griese et al., *Respir Res* 6, 80 (2005)
29. M. W. Pfaffl, G. W. Horgan, L. Dempfle, *Nucleic Acids Res* 30, e36 (May 1, 2002)

The invention claimed is:

1. A method of decreasing binding of a polyribonucleotide to retinoic acid-inducible gene I (RIG-1), comprising
producing a polyribonucleotide that encodes a protein or protein fragment by in vitro transcription using a reaction mixture comprising ATP, CTP, GTP and UTP, wherein at least 5% and not more than 50% of the UTP in the reaction mixture comprises the analog 5-iodouridine (I5U), and wherein at least 5% and not more than 50% of the CTP in the reaction mixture comprises an analog selected from the group consisting of 2'-amino-2'-deoxycytidine (C2'NH2), 2'-fluoro-2'-deoxycytidine (C2'F), and 5-iodocytidine (I5C), wherein the analog of UTP and the analogs of CTP are selected to minimize binding of the polyribonucleotide to RIG-1, and wherein the remainder of the ATP, CTP, GTP and UTP does not include a modified nucleoside;
providing the polyribonucleotide so produced; and
administering the polyribonucleotide to a subject or cell, wherein the protein or protein fragment encoded by the polyribonucleotide is expressed in the subject or cell, and wherein the polyribonucleotide has decreased binding to RIG-1 relative to a control polyribonucleotide that does not comprise the analogs.

2. The method of claim 1, wherein the polyribonucleotide includes a micro-RNA binding site.

3. The method of claim 2, wherein the polyribonucleotide includes a 3' polyA tail, and wherein the micro-RNA binding site is 3' to the sequence which encodes a protein or protein fragment and 5' from the polyA tail.

4. The method of claim 1, further comprising encapsulating said polyribonucleotide in a nanoparticle or nanocapsule.

5. The method of claim 1, further comprising encapsulating said polyribonucleotide in a cationic lipid, cationic polymer, or nanoemulsion.

6. The method of claim 1, wherein 15% to 30% of the UTP in said reaction mixture are analogs of UTP.

7. The method of claim 1, wherein 15% to 30% of the CTP in said reaction mixture are analogs of CTP.

* * * * *

SEQUENCE LISTING

```
<160> NUMBER OF SEQ ID NOS: 3

<210> SEQ ID NO 1
<211> LENGTH: 868
<212> TYPE: DNA
<213> ORGANISM: Artificial Sequence
<220> FEATURE:
<223> OTHER INFORMATION: Description of artificial sequence note =
      synthetic construct

<400> SEQUENCE: 1
```

```
ggatccatgg cctcctccga ggacgtcatc aaggagttca tgcgcttcaa ggtgcgcatg        60
gagggctccg tgaacggcca cgagttcgag atcgagggcg agggcgaggg ccgcccctac       120
gagggcaccc agaccgccaa gctgaaggtg accaagggcg gcccctgcc cttcgcctgg        180 gacatcctgt cccccagtt ccagtacggc tccaaggtgt acgtgaagca ccccgccgac        240
atccccgact acaagaagct gtccttcccc gagggcttca gtgggagcg cgtgatgaac       300 ttcgaggacg gcggcgtggt gaccgtgacc caggactcct ccctgcagga cggctgcttc       360
atctacaagg tgaagttcat cggcgtgaac ttcccctccg acggccccgt aatgcagaag      420
aagactatgg gctgggagcc ctccaccgag cgcctgtacc cccgcgacgg cgtgctgaag     480
ggcgagatcc acaaggccct gaagctgaag gacgcggcc actacctggt ggagttcaag      540
tccatctaca tggccaagaa gcccgtgcag ctgcccggct actactacgt ggactccaag      600
ctggacatca cctcccacaa cgaggactac accatcgtgg agcagtacga gcgcgccgag      660
ggccgccacc acctgttcct gtagctagag tcgactccat aaagtaggaa acactacacg      720
attccataaa gtaggaaaca ctacaaccgg ttccataaag taggaaacac tacatcactc      780
cataaagtag gaaacactac acaaaaaaaa aaaaaaaaaa aaaaaaaaaa aaaaaaaaaa      840
aaaaaaaaaa aaaaaaaaaa aagatatc                                          868

<210> SEQ ID NO 2
<211> LENGTH: 18
<212> TYPE: DNA
<213> ORGANISM: Artificial Sequence
<220> FEATURE:
<223> OTHER INFORMATION: Description of artificial sequence note =
      synthetic construct

<400> SEQUENCE: 2
gcacccagac cgccaagc                                                       18

<210> SEQ ID NO 3
<211> LENGTH: 19
<212> TYPE: DNA
<213> ORGANISM: Artificial Sequence
<220> FEATURE:
<223> OTHER INFORMATION: Description of artificial sequence note =
      synthetic construct

<400> SEQUENCE: 3
atctcgccct tcagcacgc                                                      19
```